US010155015B2

(12) United States Patent
Mazo et al.

(10) Patent No.: US 10,155,015 B2
(45) Date of Patent: Dec. 18, 2018

(54) PROBIOTIC COMPOSITIONS FOR USE IN THE TREATMENT OF BOWEL DISEASES

(71) Applicants: Jordi Espadaler Mazo, Girona (ES); Jordi Cune Castellana, Bellaterra (ES)

(72) Inventors: Jordi Espadaler Mazo, Girona (ES); Jordi Cune Castellana, Bellaterra (ES)

(73) Assignee: AB-Biotics S.A., Barcelona (ES)

( * ) Notice: Subject to any disclaimer, the term of this patent is extended or adjusted under 35 U.S.C. 154(b) by 0 days.

(21) Appl. No.: 15/134,558

(22) Filed: Apr. 21, 2016

(65) Prior Publication Data
US 2016/0220620 A1 Aug. 4, 2016

Related U.S. Application Data

(63) Continuation of application No. 13/575,865, filed as application No. PCT/EP2011/051170 on Jan. 27, 2011, now abandoned.

(60) Provisional application No. 61/299,116, filed on Jan. 28, 2010.

(30) Foreign Application Priority Data

Jan. 28, 2010 (EP) .................................... 10151998

(51) Int. Cl.
*A61K 35/747* (2015.01)
*A61K 35/76* (2015.01)
*A61K 35/74* (2015.01)
*A61K 35/744* (2015.01)
*A23L 33/135* (2016.01)

(52) U.S. Cl.
CPC .......... *A61K 35/747* (2013.01); *A23L 33/135* (2016.08); *A61K 35/74* (2013.01); *A61K 35/744* (2013.01); *A23V 2002/00* (2013.01); *A23Y 2220/67* (2013.01); *A23Y 2280/15* (2013.01)

(58) Field of Classification Search
None
See application file for complete search history.

(56) References Cited

U.S. PATENT DOCUMENTS

| 7,195,906 | B2 | 3/2007 | Collins et al. ............. 435/252.1 |
| 7,842,495 | B2 | 11/2010 | Yamahira et al. ......... 435/252.9 |
| 8,298,526 | B2* | 10/2012 | Leu ........................ C12R 1/225 424/93.1 |
| 8,309,075 | B2 | 11/2012 | Albers et al. ............. 424/93.45 |
| 8,420,376 | B2* | 4/2013 | Alenfall ................. A21D 2/267 435/252.9 |
| 9,168,267 | B2* | 10/2015 | Vriesema ............. A61K 31/702 |
| 9,254,303 | B2* | 2/2016 | Sprenger ................. A23L 33/21 |
| 9,861,666 | B2* | 1/2018 | Griffiths ............... A61K 35/747 |
| 2002/0114786 | A1 | 8/2002 | Fabre et al. ................ 424/93.3 |
| 2010/0196323 | A1 | 8/2010 | Plail et al. |

FOREIGN PATENT DOCUMENTS

| EP | 0415941 | 6/1993 |
| EP | 0554418 | 8/1993 |
| WO | WO 96/29083 | 9/1996 |
| WO | WO 2004/110466 A2 | 12/2004 |
| WO | WO 2007/150052 A1 | 12/2007 |
| WO | WO 2010/114864 A1 | 10/2010 |

OTHER PUBLICATIONS

Daniel et al Selecting Lactic Acid Bacteria for Their Safety and Functionality by Use of a Mouse Colitis ModelApplied and Environmental Microbiology, Sep. 2006, p. 5799-5805.*
Hou et al Clinical Gastroenterology and Hepatology vol. 12, Issue 10, Oct. 2014, pp. 1592-1600 Abstract.*
De Ceglie et al., Acute small bowel obstruction caused by endometriosis: A case report and review of the literatureWorld J Gastroenterol Jun. 7, 2008; 14(21): 3430-3434.*
Macfarlane et al. Probiotics and prebiotics: can regulating the activities of intestinal bacteria benefit health?BMJ vol. 318 Ap. 10, 1999 pp. 999-1003.*
Mims et al., Medical Microbiology, Third Edition. Mosby Elsenvier Science. pp. 214-215, 246-247, 194-196, 270-271.*
Mims et al., Medical Microbiology, Third Edition. Mosby Elsenvier Science. pp. 280-284.*
Tedeling et al., Anti-inflammatory properties of the short-chain fatty acidsacetate and propionate: A study with relevance to inflammatory bowel diseaseWorld J Gastroenterol May 28, 2007; 13(20): 2826-2832.*
Russell-Jones G.J. Oral vaccine deliveryJ. Control Release 65 (2000), pp. 49-54.*
Reid et al., Probiotic Lactobacillus dose required to restore and maintain a normal vaginal flora. FEMS Immunol Med Microbiol. Dec. 2001;32(1):37-41.*
Biomass—Wikipedia pp. 1-12, dowloaded on Mar. 23, 2018.*
Agrawal, A., et al., Fermented milk containing the probotic bifidobacterium animalls, Gastroenterology, Elsevier, 134(4)(1):546, (2008).
Barouel, J., et al., "Prophylactic role of maternal administration of probiotics in the prevention of irritable bowel symdrome," Medical Hypotheses 73(5):764-767 (2009).
WPI Database Abstract for JP 2008-013534 (2008).
Hart A. L., et al., "Use of probiotics in the treatment of inflammatory bowel disease." Journal of Clinical Gastroenterology, 36(2):111-119 (2003).
Jonkers, D., et al., "Probiotics and inflammatory bowel disease," Journal of the Royal Society of Medicine, 96(4):167-171 (2003).

(Continued)

Primary Examiner — Maria G Leavitt
(74) Attorney, Agent, or Firm — Finnegan, Henderson, Farabow, Garrett & Dunner LLP

(57) ABSTRACT

The present disclosure is directed to methods of administering and compositions comprising *Lactobacillus plantarum* CECT 7478, *Lactobacillus plantarum* CECT 7485, and *Pediococcus acidilactici* CECT 7483 or a mutant or variant thereof. The compositions and methods are useful in the probiotic treatment of bowel diseases or conditions such as Inflammatory Bowel Disease, Irritable Bowel Syndrome, and abdominal distension and bloating.

23 Claims, 6 Drawing Sheets

Specification includes a Sequence Listing.

(56) References Cited

OTHER PUBLICATIONS

Shanahan, Fergus, "Probiotics in inflammatory bowel disease—therapeutic rationale and role," Advanced Drug Delivery Reviews, 56(6):809-818 (2004).
Extended European Search Report for European Application No. 10151998.1, dated Jul. 8, 2010.
International Search Report for PCT Application No. PCT/EP2011/051170 (WO 2011/092261), dated Mar. 15, 2011.
Written Opinion of the International Searching Authority for PCT Application No. PCT/EP2011/051170 (WO 2011/092261), dated Mar. 15, 2011.
Altschul, S.F., et al. "Basic local alignment search tool", J. Mol. Biol., 1990, vol. 215, p. 403-410.
Anadón, A., et al. "Opinion of the Scientific Panel on Additives and Products or Substances used in Animal Feed on the updating of the criteria used in the assessment of bacteria for resistance to antibiotics of human veterinary importance", The EPSA Journal, 2005, vol. 233, p. 1-12.
Andreoletti, O., et al. "The maintenace of the list of QPS microorganisms intentionally added to food or feed. Question No. EFSA-Q-2008-006", The EFSA Journal, 2008, vol. 923, p. 1-48.
Araya, M., et al. (2002) Guidelines for the Evaluation of Probiotics in Food—Joint FAO/WHO Working Group. FAO/WHO, Ontario, Canada.
Badia, X., et al. "Adaptación al español del cuestionarlo IBSQoL para la medición de la calidad de vida en pacientes con síndrome de intestino irritable.", Rev Esp Enferm Dig. 2000, vol. 92, p. 637-643.
Bories, G., et al. "Update on the criteria used in the assessment of bacterial resistance to antibiotics of human or veterinary importance", The EFSA Journal, 2008, vol. 732, p. 1-15.
Collado, M., et al. "Probiotic Strains and Their Combination Inhibit In Vitro Adhesion of Pathogens to Pig Intestinal Mucosa", Current Microbiology, 2007, vol. 55, p. 260-265.
Cooper, H.S., et al. "Clinicopathologic study of dextran sulfate sodium experimental murine colitis", Lab Invest., 1993, vol. 69, p. 236-249.
D'Argenio, G. and Mazzacca, G. "Short-chain fatty acid in the human colon. Relation to inflammatory bowel diseases and colon cancer", Adv Exp Med Biol, 1999, vol. 472, p. 149-158.
Daniel, C., et al. "Selecting Lactic Acid Bacteria for Their Safety and Functionality by Use of a Mouse Colitis Model", Appl. Environ. Microbiol, 2006, vol. 72, p. 5799-5805.
Dean, B.B., et al. "Impairment in work productivity and health-related quality of life in patients with IBS", Am J Manaq Care., 2005, vol. 11, p. S17-26.
Fitzpatrick, L.R., et al. "Effects of the probiotic formulation VSL#3 on colitis in weanling rats", J Pediatr Gastroenterol Nutr., 2007, vol. 44, p. 561-570.
Fukumoto, S., et al. "Short-chain fatty acids stimulate coloonic transit via intraiuminal 5-HT release in rats", Am J Physiol Regul Integr Comp Physiol, 2003, vol. 284, p. R1269-R1276.
Grabig, A., et al. "Escherichia coli Strain Nissle 1917 Ameliorates Experimental Colitis via Toll-Like Receptor 2- and Toll-Like Receptor 4-Dependent Pathways", Infect. Immun., 2006, vol. 74, p. 4075-4082.
Guarner, F. and Schaafsma, G.J. "Probiotics", Int J Food Microbiol., 1998, vol. 39, p. 237-238.
Hahn, B.A., et al., "Evaluation of a new quality of life questionnaire for patients irritable bowel syndrome", Ailment Pharmacol Ther, 1997, vol. 11, p. 547-52, and copy of IBSQOL surey discussed therein.
Jacobsen, C.N., et al. "Screening of Probiotic Activities of Forty-Seven Strains of Lactobacillus spp. by In Vitro Techniques and Evaluation of the Colonization Ability of Five Selected Strains in Humans", Appl. Environ. Microbiol., 1999, vol. 65, p. 4949-4956.
Katz, J., A. "Management of inflammatory bowel disease in adults", Journal of Digestive Diseases, 2007, vol. 8, p. 65-71.
Labus, J.S., et al. "The Visceral Sensitivity Index: development and validation of a gastrointestinal symptom-specific anxiety scale", Alimentary Pharmacology & Therapeutics, 2004, vol. 20, p. 89-97.
Longstreth, G.F., et al. "Functional Bowel Disorders", Gastroenterology, 2006, vol. 130, p. 1480-1491.
Maslowski, K.M., et al, "Regulation of inflammatory responses by gut microbiota and chemoattractant receptor GPR43", Nature, 2009, vol. 461, p. 1282-1286
Okayasu, I., et al. "A novel method in the induction of reliable experimental acute and chronic ulcerative colitis in mic", Gastroenterology., 1990, vol. 98, p. 694-702.
Pathmakanthan, S., et al. "Lactobacilius plantarum 299: Beneficial in vitro immunomodulation in cells extracted from inflamed human colon", Journal of Gastroenterology and Hepatology, 2004, vol. 19, p. 166-173.
Rezaie, A., et al. "Oxidative Stress and Pathogenesis of Inflammatory Bowel Disease: An Epiphenomenon or the Cause?", Digestive Diseases and Sciences, 2007, vol. 52, pp. 2015-2021.
Rodas, A.M., et al. "Polyphasic study of wine Lactobacillus strains: taxonomic implications", Int J Syst Evol Microbiol, 2005, vol. 56, p. 197-207.
Roessner, A., et al. "Oxidative stress in ulcerative colitis-associated carcinogenesis", Pathol Res Pract., 2008, vol. 204, p. 511-524.
Sasaki, M., et al. "Reversal of experimental Colitis disease activity in mice following administration of an adenoviral IL-10 vector", Journal of Inflammation, 2005, vol. 2, p. 13.
Scheinin, T., et al. "Validation of the interleukin-10 knockout mouse model of colitis: antitumour necrosis factor-antibodies suppress the progression of colitis.", Clin Exp Immunol, 2003, vol. 133, p. 38-43
Tazoe, H., et al. "Roles of short-chain fatty acids receptors, GPR41 and GPR43 on colonic functions", J Physiol Pharmacol., 2008 vol. 59, p. 251-262,
Tedelind, S., et al. "Anti-inflammatory properties of the short-chain fatty acids acetate and propionate: a study with relevance to inflammatory bowel disease", World J Gastroenterol, 2007, vol. 13, p, 2826-2832.
Vanhoutvin, S.A., et al. "The Effects of butyrate enemas on visceral perception in healthy volunteers", Neurogastroenterology & Motility 2009, vol. 21, p. 952-e976.
Wang, Q., et al. "Naive Bayesian Classifer for Rapid Assignment of rRNA Sequences into the New Bacterial Taxonomy", Appl. Environ. Microbiol., 2007, vol. 73, p. 5261-5267.
Weisburg, W.G., et al. "16S ribosomal DNA amplification for phylogenetic study", J. Bacteriol., 1991, vol. 173, p. 697-703.
Yamada, Y., et al. "A comparative analysis of two models of colitis in rats", Gastroenterology, 1992, vol. 102, p. 1524-1534.
Zhang, L., et al. "Alive and Dead Lactobacillus rharnhosus GG Decrease Tumor Necrosis Factor-alpha-Induced Interleukin-8 Production in Caco-2 Cells", J. Nutr., 2005 vol. 135, p. 1752-1756.
Decision to grant a European patent pursuant to Article 97(1) EPC in related Europan Application No. 11702426.5, dated Oct. 17, 2013 (pp. 1-2), and allowed claims (pp. 3-4).
Hijova et al., Bratisl Lek Listy 2007; 108 (8): 354-3.58 Topical Review Short chain fatty acids and colonic health.
Ngo, In the Protein Folding Problem and Tertiary Structure Prediction, Merz et al. (eds.), Birkhauser Boston: Boston, MA, pp. 433 and 492-495, 1994.
Kimchi-Sarfaty et al., Science, pp. 525-528, 2007.
Voet, Biochemistry, John Wiley and Sons, pp. 126-129, 1990.
Chen, Shyr-Chyr et al., "Nonsurgical management of partial adhesive small-bowel obstruction with oral therapy: a randomized controlled trial," Canadian Medical Association Journal (CMAJ), 173(10):1165-69 (2005).

* cited by examiner

FIG. 1 (Continuation)
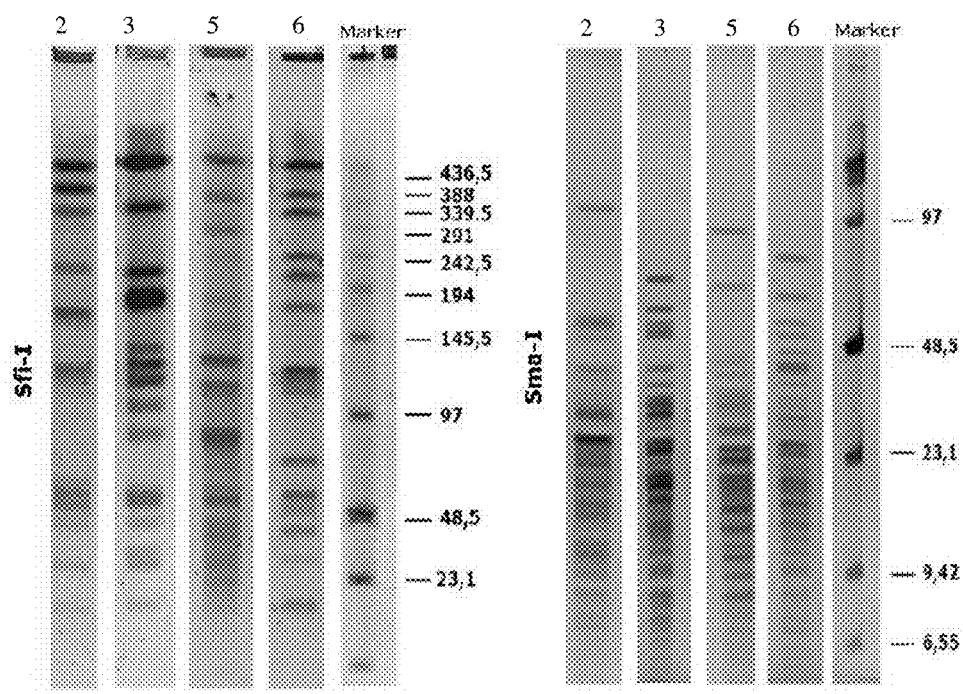

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: forward Eub27f primer

<400> SEQUENCE: 1
agagtttgat cctggctcag                                              20

<210> SEQ ID NO 2
<211> LENGTH: 19
<212> TYPE: DNA
<213> ORGANISM: Artificial
<220> FEATURE:
<223> OTHER INFORMATION: reverse Eub1492r primer

<400> SEQUENCE: 2
ggttaccttg ttacgactt                                               19

<210> SEQ ID NO 3
<211> LENGTH: 57
<212> TYPE: DNA
<213> ORGANISM: Artificial
<220> FEATURE:
<223> OTHER INFORMATION: forward 357f primer

<400> SEQUENCE: 3
```

```
cgcccgccgc gcccgcgcc cggcccgccg ccccgcccc cctacgggag gcagcag        57

<210> SEQ ID NO 4
<211> LENGTH: 20
<212> TYPE: DNA
<213> ORGANISM: Artificial
<220> FEATURE:
<223> OTHER INFORMATION: reverse 907r primer

<400> SEQUENCE: 4
ccgtcaattc ctttgagttt                                                20
```

PROBIOTIC COMPOSITIONS FOR USE IN THE TREATMENT OF BOWEL DISEASES

This application is a continuation of U.S. application Ser. No. 13/575,865, filed Jul. 27, 2012, which is a national stage filing under 35 U.S.C. § 371 of International Application No. PCT/EP2011/051170, filed on Jan. 27, 2011, which claims the benefit of the U.S. provisional application No. 61/299,116, and of the European patent application EP10151998, both filed on 28 Jan. 2010, all of which are incorporated herein by reference.

REFERENCE TO SEQUENCE LISTING SUBMITTED ELECTRONICALLY

The official copy of the sequence listing was submitted electronically via EFS-Web as an ASCII formatted sequence listing with a file named "12072-0001-Sequence_Listing.txt," created on Sep. 20, 2012, and having a size of 1.06 kilobytes and was filed on Sep. 21, 2012, in U.S. application Ser. No. 13/575,865, upon which this application relies for the benefits provided in 35 U.S.C. § 120.

The present invention relates to the fields of medicine, microbiology and nutrition and, particularly, to a novel probiotic composition. Particularly, new strains of *Lactobacillus plantarum* and *Pediococcus acidilactici* have been isolated and combined in a formulation useful in the treatment of gastrointestinal diseases, such as bowel inflammation (e.g., inflammatory bowel disease) and irritable bowel syndrome.

BACKGROUND OF THE INVENTION

Ulcerative colitis (UC), Pouchitis, and Crohn's Disease are examples of Inflammatory Bowel Diseases (IBD) characterized by chronic inflammation in the intestine. The clinical symptoms are diarrhea, abdominal pain, occasional rectal bleeding, weight loss, tiredness and sometimes fever. Although occurring at any age, IBD is most common in teenagers and young adults, which consequently may suffer from delayed development and stunted growth. The frequency of the disease is similar to type 1 diabetes in Europe and the USA. The clinical course of IBD varies considerably. Patients with mild to moderate symptoms may be treated without hospitalization. However, 10-15% of patients experience a severe course of the disease, which in many cases is followed by surgery.

IBD is treated medically by reducing the inflammation and thereby controlling the gastrointestinal symptoms. However, there is currently no medical cure for IBD. Coloectomy may eliminate UC but reduces life quality and increases the risk of complications. The available medical treatments include the use of 5-aminosalicylic acid (5-ASA), corticosteroids and immunomodulatory medicaments. Prolonged treatment of mild to moderate IBD symptoms is usually carried out using 5-ASA while corticosteroids and immunomodulatory medicaments are used to treat severe symptoms. Diarrhea or abdominal pain appear as side effects of 5-ASA whereas long term use of corticosteroids frequently shows serious side effects including reduction in bone mass, infection, diabetes, muscle wasting and psychiatric disturbances. Immunomodulatory medicaments suppress the immune system, which controls the IBD symptoms. However, the resulting immuno-compromised state leaves the patient susceptible to many diseases.

Irritable Bowel Syndrome (IBS) is a condition characterized by abdominal pain and/or discomfort which is associated to altered bowel habit or defecation, where symptoms are not explained by structural or biochemical abnormalities. Urgency, bloating and feeling of incomplete bowel movements are also common in IBS. Therefore, it is classified among functional gastrointestinal disorders which include diseases such as functional bloating, noncardiac chest pain, non-ulcer dyspepsia, and chronic constipation or diarrhea (Longstreth G. H. et al., 2006). Noteworthy, IBS has a substantial impact on morbidity and quality of life beyond abdominal pain and discomfort, as the associated symptoms affect both the sufferer's sense of well-being and the ability to function normally (Dean B. B. et al., 2005).

There is a tremendous activity in the field of drug development for the treatment of IBS. In this regard, various antidepressants have gained popularity although their efficacy in clinical trials has been modest and their clinical utility is limited by untoward side effects. Serotonergic agents have demonstrated efficacy on the global symptoms of IBS. However, recent concerns about safety have severely limited their use. Therefore, the development of novel therapies for IBS is of great interest.

Probiotics are defined as "living microorganisms, which upon ingestion in certain numbers, exert health benefits beyond inherent basic nutrition" (Araya M. et al., 2002; Guarner F. et al., 1998). Several lactic acid bacteria and species from the genus *Bifidobacterium* are probiotic, which implies that they have been shown to promote a specific health effect. Probiotic bacteria must fulfil several requirements related to lack of toxicity, viability, adhesion and beneficial effects. These probiotic features are strain-dependent, even among bacteria of the same species. Therefore, it is important to find those strains that have a better performance in all probiotic requirements. Human clinical trials using probiotics alone or in combination with antibiotics have been performed to identify strains and/or formulations for the treatment of patients with IBD or IBS, or for keeping already treated IBD patients in remission. WO 96/29083 and EP 554418 disclose two intestine colonizing *Lactobacillus* strains including *Lactobacillus plantarum* 299v (DSM 6595) and *Lactobacillus casei* ssp. *rhamnosus* 271 (DSM 6594). EP 415941 discloses methods for preparing nutrient composition comprising treatment of oat gruel with enzymes before mixing with lactobacilli. U.S. Pat. No. 7,195,906 discloses a strain of *Bifidobacterium* isolated from resected and washed human gastrointestinal tract for the treatment of inflammatory diseases, especially gastrointestinal inflammatory activity, such as IBD, and IBS.

In spite of a promising potential, a considerably improvement of the effect of probiotics for use in the treatment of inflammation bowel diseases (such as IBD) as well as of other gastrointestinal diseases (such as IBS) is needed.

SUMMARY OF THE INVENTION

The inventors of the present invention have found that a composition comprising *Lactobacillus* and *Pediococcus* strains is effective in the treatment of bowel inflammation. Particularly, three new probiotic strains belonging to *Lactobacillus plantarum* genus and *Pediococcus acidilactici* genus have been isolated, said strains allowing the efficient treatment of the bowel inflammation when combined into the form of a single formulation.

Thus, in a first aspect the present invention provides a composition comprising an effective amount of *Lactobacillus plantarum* CECT 7484, *Lactobacillus plantarum* CECT 7485, and *Pediococcus acidilactici* CECT 7483, or mutants or variants thereof.

*Lactobacillus plantarum* strains CECT 7485 and CECT 7484, and *Pediococcus acidilactici* strain CECT 7483 were deposited in the Spanish Type Culture Collection (Valencia, Spain) on Apr. 2, 2009. All three deposited strains are viable and keep all their features related to their deposit.

The term "effective amount" as used herein, means an amount of an active agent high enough to deliver the desired benefit, but low enough to avoid serious side effects within the scope of medical judgment.

It is clear that by using the deposited strains as starting material, the skilled person in the art can routinely, by conventional mutagenesis or re-isolation techniques, obtain further mutants or derivatives thereof that retain or enhance the herein described relevant features and advantages of the strains forming the composition of the invention. The skilled person in the art will decide upon the adequate method to be employed for determining the anti-inflammatory, immunomodulatory or anti-IBS or anti-abdominal bloating activity of the strains. Examples of possible methods to measure this activity are shown in the examples below.

In one embodiment, the mutant is a genetically modified mutant.

In another embodiment of the first aspect of the invention, the variant is a naturally occurring variant.

The strains forming part of the composition of the first aspect of the invention may be in the form of viable cells. Alternatively, the strain may be in the form of non-viable cells.

The general use of strains *P. acidilactici* CECT 7483, as well as of *L. plantarum* CECT 7484 and CECT 7485 are in the form of viable cells. However, it could also be extended to non-viable cells such as killed cultures or compositions containing beneficial factors produced by *P. acidilactici* CECT 7483, as well as of *L. plantarum* CECT 7484 and CECT 7485. This could include thermally killed micro-organisms or micro-organisms killed by exposure to altered pH, sonication, radiation or subjection to pressure. With non-viable cells product preparation is simpler, cells may be incorporated easily into pharmaceuticals and storage requirements are much less limited than viable cells.

When used in the form of the composition of the invention, the strains are, preferably, in a concentration ratio of 1:1:1.

Strains CECT 7483, CECT 7484, and CECT 7485 display a significant inhibitory activity against several pathogenic and potentially pathogenic bacterial strains, while displaying minimal antagonism against common commensal strains of the human gastrointestinal flora. Moreover, these three strains show a lack of significant inhibitory activity between them, thus allowing their combined use in a single formula. This is of relevance because this means that the composition as defined in the first aspect of the invention exerts a beneficial effect in the intestine owing to the "intact" effect of each one of the three strains. The combination of these strains into a single formula (i.e. the composition of the invention) displays the ability to improve clinical symptoms (such as weight loss and diarrhoea) in different animal models of bowel inflammation. In line with these results, the composition of the invention shows the unique ability to significantly reduce acute (IL-6) and chronic (IFNγ) cytokines.

A wide variety of lactic acid bacterial species have a long history of apparent safe use. The European Food Safety Authority has developed a system granting the "Qualified Presumption of Safety" (QPS) status to taxonomical units with a proven long history of apparent safe use. Strains CECT 7483, CECT 7484 and CECT 7485 belong to bacterial species that have QPS status (Andreoletti O. et al., 2008).

The strains of the present invention have the advantage that they are particularly useful as probiotics. As mentioned above, probiotic bacteria must fulfil several requirements related to lack of toxicity, viability, adhesion and beneficial effects. These probiotic features are strain-dependent, even among bacteria of the same species. Therefore, it is important to find those strains that have a better performance in all probiotic requirements. The examples bellow provide (by way of example) protocols to determine each one of the probiotic features and it is also demonstrated that said strains have excellent probiotic features.

The emergence and spread of resistance to antimicrobials in bacteria pose a threat to human and animal health and present a major financial and societal cost. When resistance to an antimicrobial is inherent to a bacterial species, it is generally referred to as 'intrinsic resistance' (sometimes called 'natural resistance'). Intrinsic resistance is presumed to present a minimal potential for horizontal spread, whereas acquired resistance mediated by added genes is considered as having a high potential for lateral spread. The inventors of the present invention have found that the strains forming the composition of the invention do not display any significant resistance to antibiotics of human and/or veterinary importance (ampicillin, gentamicin, streptomycin, erythromycin, tetracycline, clindamycin, and chloramphenicol) according to the guidelines of the European Food Safety Authority (Anadón A. et al., 2005; Bories G. et al., 2008), thus precluding the risk of a potential transfer of antibiotic resistance to pathogenic species.

Additionally, the inventors of the present invention have found that the strains CECT 7483, CECT 7484, and CECT 7485 can be co-administered with other medicaments used for the treatment of IBD (such as mesalazine). As it is shown below, the growth of said strains is not completely inhibited even using saturated concentrations of mesalazine. In other words, even using high concentrations of mesalazine the efficacy of composition of the invention comprising the probiotic strains is not compromise and, therefore, it can exert both the probiotic and anti-inflammation functions.

The strains of the invention have demonstrated to be highly resistant to the conditions of the gastrointestinal environment of mammals (acidic environment, bile salts, and high lysozyme, and oxygen peroxide concentrations), thus being able to survive passage through the gastrointestinal tract (hereinafter also referred as "GIT"). The strains also have good adhesion to the intestinal epithelium, which allows them to remain in the intestinal tract and to exert their probiotic effects.

Further, the present strains have several beneficial effects in the host. In addition to the anti-inflammatory activity in bowel, they benefit the intestinal microbiota balance due to their antagonistic activity. The term "antagonistic activity" refers to the inhibition of growth of gastrointestinal non-beneficial bacteria by the activity of probiotic bacteria. The condition of having inadequate gastrointestinal microbial balance is known as disbiosis and has multiple negative consequences for human well-being. It will be shown below that the strains have a high capacity to inhibit the growth of pathogenic strains when compared to other commercial strains. Additionally, as mentioned above, the inventors have found that the new strains of the invention do not display significant inhibitory activity among them.

Additionally, it has been found that the strains forming the composition of the first aspect of the invention produce large quantities of short chain fatty acids (SOFA). Production of SOFA from non-digestible fibres is an interesting probiotic trait. This trait is desirable in a probiotic because the produced SOFA shows several beneficial properties in the host. Among their various properties, SCFAs, especially butyric acid, are readily absorbed by intestinal mucosa, stimulate sodium and water absorption in the colon, and are trophic to the intestinal mucosa (D'Argenio G. et al., 1999; Tedelind S. et al., 2007). Moreover, butyric acid is used as fuel by colonocytes. Each strain in the formula is a strong producer of a different SOFA, either acetic, propionic or butyric, which are the three major SCFAs found in the intestine. The better understanding of how short chain fatty acids act on inflammation process can help in improving the efficacy of current bowel inflammation treatments. In this regard, it has been reported the relation between SCFAs and the regulation of inflammatory conditions through G protein-coupled receptors (Maslowski K. M. et al., 2009).

Furthermore, the strains CECT 7483, CECT 7484 and CECT 7485 promote immunomodulatory effects in the host, since they induce an improved cytokine pattern from the intestinal mucosa. These immunomodulatory effects are beneficial to the host because they help to achieve an improved disease resistance and diminished risk of allergies. It is known that Gram-negative bacteria in the GIT display the molecule lipopolisaccharide (LPS) in their surface, which induces the production of pro-inflammatory signals by the intestinal mucosa cells. Probiotic supplementation can change this situation to favour one greater presence of Gram positive bacteria in the GIT (grouped in the lactic acid bacteria group), with better ecologic fitness or with antagonistic properties against some Gram negative microorganisms. Nevertheless, some probiotic microorganisms show the ability to modulate per se the production of cytokines, which are messenger molecules that regulate the inflammatory and immune responses in the body. Particularly, some probiotic bacteria induce a better balanced pattern between pro/anti-inflammatory signalling in the intestinal mucosa (regardless of the effect on Gram negative bacteria). As will be illustrated below, it was found that the composition's strains of the invention promote a reduction of inflammatory cytokines (IFN-γ and IL-6) levels, thus inducing an improved cytokine pattern from the intestinal mucosa. This immunomodulatory effect is complemented by the strain's antagonistic properties in reducing the presence of pathogenic Gram negative bacteria in the GIT.

It is known that non-viable bacteria as well as bacterial components can have immunomodulatory effects per se. For instance, cell components of Lactobacilli species have been reported to induce anti-inflammatory cytokines (Pathmakanthan S. et al., 2004) or to reduce pro-inflammatory cytokines (Zhang L. et al., 2005). Upon isolation of these components, pharmaceutical grade manipulation is anticipated.

Considering the results shown below, it is clear that the strains CECT 7483, CECT 7484 and CECT 7485, forming the composition of the first aspect of the invention, are characterized by specific traits such as: survival to gastrointestinal passage, adherence to intestinal mucosa, resistance to oxidative stress, production of metabolites with anti-inflammatory activity (either short chain fatty acids or other products with said activity) and absence of antagonism between them. The composition and isolated strains of the present invention are not obviously derived from the prior art because they are the result of a complex investigation and the results which have been obtained regarding the bowel inflammation activity are surprising. Protocols for determining each one of said traits are included below. From the content of the present application, the skilled in the art could find other strains belonging to *Lactobacillus* and *Pediococcus* genus, and more particularly to *Lactobacillus plantarum* and *Pediococcus acidilactici* species which, when administered separately or combined into a single composition, show the same probiotic and therapeutic effects than those described in the present application.

In a second aspect, the invention provides a composition comprising an effective amount of the strains of the invention, or mutant strains thereof, for use as a medicament.

Particularly, it has been found that the composition comprising the strains CECT 7483, CECT 7484 and CECT 7485 has an anti-inflammatory activity in bowel in IBD models. As explained above, bowel inflammation is one of the main characteristics of IBD. Thus, the composition of the first aspect of the invention is useful in the prevention or treatment of said disease.

Therefore, in a third aspect, the invention provides the composition as defined in the first aspect of the invention for use in the prevention or treatment of bowel inflammation in an animal, including a human. This aspect can be alternatively formulated as the use of a composition as defined in the first aspect of the invention for the manufacture of a medicament for the prevention and/or treatment of bowel inflammation. This may be alternatively formulated as a method for the prevention and/or treatment of bowel inflammation in an animal, including a human, comprising administering to said animal in need thereof an effective amount of the composition as defined in the first aspect of the invention.

In one embodiment of the third aspect of the invention, the composition is used for the treatment or prevention of Inflammatory Bowel Disease.

From the data obtained using the IBD models reported in the examples (see below), it is derived that the administration of the strains of the invention, which are effective in the treatment of conditions characterized by bowel inflammation and diarrhea, can also be useful to treat other conditions characterised by inflammation of the bowel mucosa or submucosa and where diarrhea is prevalent, such as enteritis caused by radiotherapy or chemotherapy. Enteritis is a common side effect of abdominal and pelvic radiotherapy, affecting 60-70% of patients. Enteritis can force schedule changes in the radiotherapy regime to decrease side-effects, potentially leading to sub-optimal anti-tumoral efficacy of the treatment. There are currently no preventive strategies for radiotherapy-induced enteritis. However, some probiotics have shown to be promising in randomized clinical trials (RCTs). A probiotic composition, such as the one of the present invention, combining the health-promoting effects of SCFAs production, the ability to withstand reactive oxygen and nitrogen species found in the inflamed mucosa, and the antimicrobial activity against opportunistic pathogens can be useful to treat radiotherapy and chemotherapy-induced enteritis.

On the other hand, the present inventors have found that the strains of the present invention are efficient in the treatment of IBS. As it is shown below, the composition of the first aspect of the invention is useful in treating IBS, as assessed by a randomized double-blind placebo-controlled intervention trial.

Therefore, in a fourth aspect the present invention provides the composition of the first aspect of the invention for use in the prevention and/or treatment of IBS. This aspect can be alternatively formulated as the use of a composition as defined in the first aspect of the invention for the manufacture of a medicament for the prevention and/or treatment of IBS. This may be alternatively formulated as a method for the prevention and/or treatment of IBS in an animal, including a human, comprising administering to said animal in need thereof an effective amount of the composition as defined in the first aspect of the invention.

Furthermore, the present inventors have found that due to the features of the strains, the composition of the first aspect of the invention is useful in the treatment of abdominal bloating and distension. As it is shown below, when the composition of the invention is administered to people suffering from abdominal bloating and distension, it is observed a surprising improvement.

Therefore, in a fifth aspect the present invention provides the composition of the first aspect of the invention for use in the treatment of abdominal bloating and distension. This aspect can be alternatively formulated as the use of a composition as defined in the first aspect of the invention for the manufacture of a medicament for the treatment of abdominal bloating and distension. This may be alternatively formulated as a method for the treatment of abdominal bloating and distension in an animal, including a human, comprising administering to said animal in need thereof an effective amount of the composition as defined in the first aspect of the invention.

The surprising beneficial effects observed in people suffering from IBS, and/or abdominal bloating and distension may be due to the fact that the strains of the invention CECT 7483, CECT 7484 and CECT 7485 have the ability of producing the SCFAs listed in Table 6 and the antagonistic activity shown in Table 3.

It is well-known in the state of the art that SCFAs modulate gut motility. Particularly, SCFAs are known to stimulate serotonin (5-HT) release in rat colon (Fukumoto S. et al., 2003; Tazoe H. et al., 2008) which plays a pivotal role in the regulation of both gut motility and sensation. Similarly, butyric acid has been described to decrease visceral sensitivity of the intestine in human volunteers (Vanhoutvin S. A. et al., 2009). From this, it can be concluded that the strains forming the composition of the invention can be useful to treat, not only IBS or abdominal pain, but also other conditions related to gastrointestinal motility and/or gastrointestinal pain, such as functional constipation or functional diarrhoea.

The composition and isolated strains of the present invention are not obviously derived from the prior art because they are the result of a complex investigation and the results which have been obtained regarding the efficiency in the treatment of IBS and abdominal bloating and distension are surprising.

Surprisingly, the present inventors have found, for the first time, a *Pediococcus acidilactici* strain with the ability of treating IBD and IBS. Said ability, without being bound the theory, is believed to be due to the specific properties, pointed out throughout the specification, of the isolated *Pediococcus* strain. In the light of the teachings and protocols provided in the present specification, the skilled person in the art will be able to find further *P. acidilactici* strains with the same probiotic and therapeutic features than the one object of the present application.

The composition according to the invention that comprises an effective amount of the strains of the invention, or of their mutants, can be formulated as edible, pharmaceutical or veterinary products, in which said strains are the only active agents or are mixed with one or more other active agents and/or are mixed with pharmaceutically or veterinary acceptable excipients (in the case of a pharmaceutical or veterinary product) or adequate additives (in the case of an edible product). In a particular embodiment of the invention, the products additionally contain one or more further active agents. Preferably, the additional active agent or agents are other probiotic bacteria which are not antagonic to the strains forming the composition of the invention. Depending on the formulation, the strains may be added as purified bacteria, as a bacterial culture, as part of a bacterial culture, as a bacterial culture which has been post-treated, and alone or together with suitable carriers or ingredients. Prebiotics could be also added.

In other aspects the invention provides a pharmaceutical and veterinary products that contain an effective amount of the composition of the invention together with adequate amounts of pharmaceutically or veterinary acceptable excipients. In this regard, the pharmaceutical product may be prepared in any suitable form which does not negatively affect to the bioavailability of the strains forming the composition of the invention. Thus, the composition of the invention can be formulated to be administered orally in the form, for instance, of freeze-dried power, capsules, liquid preparations, etc. Selection of the excipients and the most appropriate methods for formulation in view of the particular purpose of the composition is within the scope of ordinary persons skilled in the art of pharmaceutical technology. Although oral administration is preferred, other forms are possible, such as injectable, rectal or topical.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts. Likewise, the term "veterinary acceptable" means suitable for use in contact with the tissues of a non-human animal.

The strains of the invention can be also included in a variety of edible products, such as a milk products, a yogurt, a curd, a cheese (e.g. quark, cream, processed, soft and hard), a fermented milk, a milk powder, a milk based fermented product, an ice-cream, a fermented cereal based product, a milk based powder, a beverage, a dressing, and a pet food. The term "edible product" is used herein in its broadest meaning, including any type of product, in any form of presentation, which can be ingested by an animal, but excluding pharmaceutical and veterinary products. Examples of other edible products are meat products (e.g. liver paste, frankfurter and salami sausages or meat spreads), chocolate spreads, fillings (e.g. truffle, cream) and frostings, chocolate, confectionery (e.g. caramel, fondants or toffee), baked goods (cakes, pastries), sauces and soups, fruit juices and coffee whiteners. Particularly interesting edible products are dietary supplements and infant formulas. In the sense of the present invention, dietary supplements also include nutraceuticals, which are known to be extracts of foods that have a medicinal effect on human health. Fodders for animal food are also included in the scope of the invention. The compositions of the invention could be also used as an ingredient in other food products.

Accordingly, in another aspect of the invention, an edible product is provided which contains the composition of the invention together with appropriate amounts of edible ingredients. Preferably, the composition of the invention is a dietary supplement.

The effective amount of colony forming units (cfu) for each strain in the composition will be determined by the skilled in the art and will depend upon the final formulation. For instance, in edible products, the strain or strains are present in an amount from about $10^5$ cfu/g to about $10^{12}$ cfu/g, preferably in an amount from about $10^7$ cfu/g to about $10^{12}$ cfu/g, according to the current legislation. The term "colony forming unit" ("cfu") is defined as number of bacterial cells as revealed by microbiological counts on agar plates.

Dietary supplements usually contain probiotic strains in an amount ranging from $10^7$ and $10^{12}$ cfu/g. In a particular embodiment, the composition of the invention is a dietary supplement comprising between $10^9$-$10^{11}$ cfu/g.

The strains of the invention are produced by cultivating the bacteria in a suitable medium and under suitable conditions. The strains can be cultivated alone to form a pure culture, or as a mixed culture together with other microorganisms, or by cultivating bacteria of different types separately and then combining them in the desired proportions. After cultivation, the cell suspension is recovered and used as such or treated in the desired manner, for instance, by concentrating or freeze-drying, to be further employed in the preparation of pharmaceutical or edible products. Sometimes the probiotic preparation is subjected to an immobilisation or encapsulation process in order to improve the shelf life. Several techniques for immobilisation or encapsulation of bacteria are known in the art.

If the composition according to the invention is used as a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, granules, powders, suspensions, sachets, pastilles, sweets, bars, syrups and corresponding administration forms, usually in the form of a unit dose. Preferably, the composition of the invention is administered in the form of tablets, capsules or powders, manufactured in conventional processes of preparing pharmaceutical products.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein.

EXAMPLES

Figure 1:
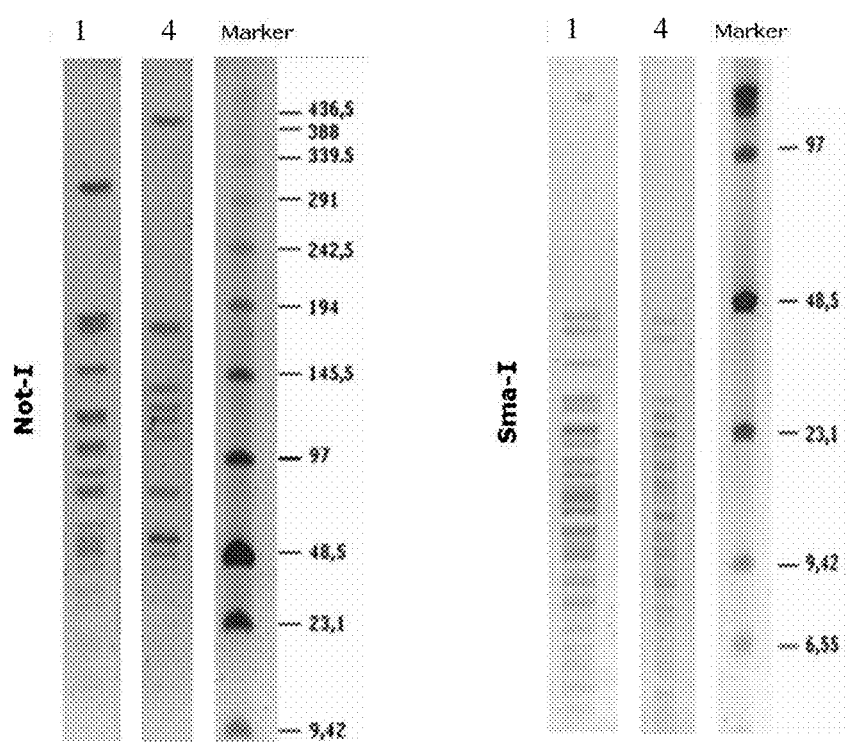
FIG. 1 represents the pulsed field gel electrophoresis patterns of Not-I or Sfi-I (left) and Sma-I (right) restricted genomic DNA of: 1, *Pediococcus acidilactici*CECT 7483; 2, *Lactobacillus plantarum* CECT 7484; 3, *Lactobacillus plantarum* CECT 7485. As controls: 4, commercial strain *P. acidilactici* Rossell11001 (Institut Rossell, Canada); 5, *L. plantarum* 299v (Probi AB, Sweden); and 6, *L. plantarum* strain isolated from commercial product VSL#3 (VSL Pharmaceuticals, USA). This Figure refers to the "strain genotyping" section.

The following sections describe the characterization of the strains of the invention, their specific probiotic features and their physiological effects on the gastrointestinal and immune systems. As used hereinafter, strain F1033 corresponds to *Pediococcus acidilactici* CETC 7483, strain F2064 to *Lactobacillus plantarum* CECT 7484, and strain F2076 to *Lactobacillus plantarum* CECT 7485.

1. Isolation of Microorganisms

A) Methods

For isolation of microorganisms, fresh stools and saliva (Daniel C. et al., 2006) were collected from 0-5 year-old children and dissolved in PBS buffer (pH 7.4), aliquoted and plated on MRS supplemented with various antibiotic combinations. Strains were cultured under microaerophilic conditions (5% $CO_2$) at 37° C. Incubation time depended on the growth rate, but run normally from 24 h to 3 days. Gram staining was carried out in order to get a first identification. Once grown, isolated strains were stored by lyophilisation in PBS 0.1× with 15% skim milk powder.

B) Results

Novel strains F2064, F2076 and F1033 were grown on MRS agar supplemented with 10 μg/ml vancomycin. Microscopic examination revealed that strains F2064 and F2076 are Gram-positive bacilli, while strain F1033 is a Gram-positive with coccal morphology.

2. Identification

A) Methods

Genomic DNA was extracted using Wizard genomic DNA purification kit (Promega). For each isolated strain, the 16S gene was amplified by PCR, using the universal primers 27f, 357f, 907r and 1492r (Weisburg W. G. et al., 1991), which generate a nearly full-length 16S rRNA fragment (1465 bp). DNA was washed using Quiaquick kit (Quiagene, GmbH, Hilden, Germany) and four sequencing reactions were performed per sample, using BigDye v.3.1 kit, on a Genetic Analyzer 3130 (Applied Biosystems). Selected sequencing primers DNA Sequence Analysis v.5.2 (Applied Biosystems) software was used to collect data and to build chromatograms, which were analyzed through Chromas (Technelysium Pty Ltd.) and BioEdit (Ibis Biosciencies) software. Genus and species identification was performed by comparison of the obtained sequence with 16S sequences of known organisms from both RefSeq data base (http://www.ncbi.nlm.nih.gov/RefSeq/) by means of a BLASTN search (Altschul S. F. et al., 1990), and from the Ribosomal Database Project (Wang Q. et al., 2007).

TABLE 1

Primers used for amplifying and sequencing the 16S gene.

| Step | Primer | Orientation | 5' → 3' Sequence |
|---|---|---|---|
| Amplification | 27f | forward | AGAGTTTGATCCTGGCTCAG (SEQ ID NO: 1) |
| | 1492r | reverse | GGTTACCTTGTTACGACTT (SEQ ID NO: 2) |
| Sequencing | 27f | forward | AGAGTTTGATCCTGGCTCAG (SEQ ID NO: 1) |
| | 357f | forward | CGCCCGCCGCGCCCGCGCCCGGCCCGC CGCCCCGCCCCCCTACGGGAGGCAGCAG (SEQ ID NO: 3) |
| | 907r | reverse | CCGTCAATTCCTTTGAGTTT (SEQ ID NO: 4) |
| | 1492r | reverse | GGTTACCTTGTTACGACTT (SEQ ID NO: 2) |

B) Results

Strains F2064 and F2076 were identified as members of the *Lactobacillus plantarum* group. Strain F1033 was identified as *Pediococcus acidilactici*.

3. Survival to GI Tract

A) Methods

To assess tolerance to acidic environment, 20-μl aliquots of each bacterial strain culture were placed in 96-well plates, together with 200-μl aliquots of MRS medium adjusted with HCl to pH 2 and 3 (Panreac). Plates were kept at 37° C. for 1 h and optical density at 620 nm was measured. Finally, viable cells were determined by plate counting and compared to the number of viable cells in the inoculum.

To assess tolerance to bile salts, 20-μl aliquots of each bacterial strain culture were placed in a 96-well plate together with 200 μl of MRS medium supplemented with 0.5% Oxgall (Sigma). Plates were incubated at 37° C. and 5% $CO_2$ for 3 hours, and then optical density was measured. Finally, viable cells were determined by plate counting and compared to the number of viable cells in the inoculum.

B) Results

All three strains displayed a good ability to survive acidic environments, with less than one log reduction in the number of viable cells after 1 h incubation in MRS at pH=2 or pH=3. Strains also posses a marked resistance to bile salts, with less than a 50% reduction in the number of viable cells after 3 h incubation in MRS supplemented with 0.5% of bile salts.

4. Adherence

A) Methods

Porcine intestine was washed with PBS pH 7.4, containing 0.01% gelatin and a cocktail of protease inhibitors (Complete®, Sigma). The mucosa was scrapped and dissolved in HEPES-Hank's buffer (10 mM HEPES, pH 7.4) (Collado M. et al., 2007) containing the aforementioned inhibitors. Then, mucus was centrifuged at 13000 rpm for 10 min using the same buffer. Supernatants were recovered and protein content was determined by Bradford protocol. 24 h before the assay, 1 ml of mucus solution 0.5 mg/ml was incubated in wells of a 24-well ELISA plate.

Each strain to be tested was grown overnight in MRS medium supplemented with tritium-labeled thymidine (5 μl in 3 ml of MRS). Cultures were centrifuged and adjusted to $10^8$ cfu/ml in PBS by counting on a Neubauer chamber and samples of each culture were taken to determine the amount of tritium-labeled thymidine incorporated by means of a scintillation reader. Then, 0.5 ml were added to the mucus-containing wells of the 24-well plate and incubated at 37° C. for 60 min. Supernatant of each well was removed, and wells were washed twice with MEM Alpha medium (Gibco) to remove loosely adherent bacteria. Finally, wells were scrapped to retrieve the mucus together with the adhering bacteria, and radioactivity was measured. Specific activity (cpm/CFU) of each culture was calculated from the total radioactivity incorporated in the PBS suspension adjusted to $10^8$ cfu/ml. *Lactobacillus rhamnosus* GG (Valio Ltd, Finland) was used as a positive control, because of its remarkable high adherence to the intestinal epithelium (Jacobsen C. N. et al., 1999).

Caco-2 cells were obtained from ATCC (ECACC No: 86010202). Cells were seeded in 24-well plates and allowed to grow in DMEM until confluence (37° C., 5% $CO_2$). The experimental procedure to obtain the number of bacteria that adhere per unit of caco-2 cells area is essentially the same as the one explained above for adhesion to mucus.

B) Results

Adhesion capacity of strains F1033, F2064 and F2076 was measured from scintillation of tritium-labeled thymidine and compared to those of the commercial strain *L. rhamnosus* GG. Adhesion to epithelial cells using the Caco-2 model is a common assay for probiotic strains.

Compared to *L. rhamnosus* GG, strains F2064 and F2076 show an affinity for epithelial cells 60% lower. However, considering the high affinity of *L. rhamnosus* GG for epithelial cells, these values are comparable to other well known probiotics such as *L. plantarum* 299v, and superior to many other probiotic strains (Jacobsen C. N. et al., 1999). On the other hand, adhesion of strain F1033 to epithelial cells is 2.5 times higher than *L. rhamnosus* GG. Besides, strains F2064 and F2076 displayed a much higher affinity for intestinal mucus than for epithelial cells, while strain F1033 showed the opposite behavior. Results are shown in the following table.

TABLE 2

Mucus adhesion of probiotic bacterial strains.
[* From a total bacteria concentration of $10^8$ cfu].

| Strain | Caco-2 (cfus/cm$^2$) | Mucus (cfus/cm$^2$) |
|---|---|---|
| F1033 | $1.21 \pm 0.17 \cdot 10^5$ cfu | $6.06 \pm 0.73 \cdot 10^4$ cfu |
| F2064 | $1.89 \pm 0.12 \cdot 10^4$ cfu | $2.25 \pm 0.12 \cdot 10^6$ cfu |
| F2076 | $1.71 \pm 0.16 \cdot 10^4$ cfu | $5.91 \pm 0.03 \cdot 10^5$ cfu |
| *L. rhamnosus* GG | $4.41 \pm 0.22 \cdot 10^4$ cfu | $3.29 \pm 0.57 \cdot 10^6$ cfu |

5. Antagonism Capacity

A) Methods

The following indicator strains were used: *P. mirabilis* CECT 4557, *K. oxytoca* CIP 103434, *C. perfringens* ATCC 13124, *C. ramosum* ATCC 25582, *E. faecalis* CETC 795, *Y. pseudotuberculosis* ATCC29833, *B. vulgatus* ATCC 8482 and *B. thetaiotaomicron* ATCC2079 were collection strains. *C. albicans*, *S. enterica* thyphimurium, *S. enterica* cholerasuis, *C. jejuni*, *E. coli* and *P. aeruginosa* were lab isolates. Indicator strains were swabbed uniformly in plates containing the appropriate medium (Oxoid) and grown to confluence at the appropriate temperatures in microaerophilic conditions (5% $CO_2$). Then, 6 mm (diameter) cylinder sections of confluent F1033, F2064 or F2076 agar plates were placed upside-down on the indicator strain plate and incubated overnight at 37° C. The next day, inhibition zones were measured by placing the agar plate over a flat rule. Growth inhibitory activity (GI) was calculated as follows:

$$GI = \frac{(IZD - CD)}{2}$$

where IZD is the Inhibition Zone Diameter and CD is the cylinder diameter, measured in millimeters.

B) Results

TABLE 3

Growth inhibitory activity (GI) of probiotic strains against 12 pathogenic or potentially pathogenic strains, and against 2 common commensal strains of the gastrointestinal flora.

| | F2064 | F2076 | F1033 |
|---|---|---|---|
| Pathogens | | | |
| *C. albicans* | 2 | 0.5 | 1.25 |
| *S. enterica typhimurium* | 1 | 1 | 0.25 |
| *S. enterica cholerasuis* | 1 | 1 | 0.5 |
| *E. coli* | 1.75 | 3.7 | 1.1 |
| *C. jejuni* | 0 | 0 | 4.75 |
| *K. oxytoca* | 0.5 | 1 | 2 |
| *P. mirabilis* | 4 | 1.5 | 0.5 |
| *P. aeruginosa* | 3 | 3.75 | 4.5 |

TABLE 3-continued

Growth inhibitory activity (GI) of probiotic strains against 12 pathogenic or potentially pathogenic strains, and against 2 common commensal strains of the gastrointestinal flora.

| | F2064 | F2076 | F1033 |
|---|---|---|---|
| *E. faecalis* | 1.75 | 1 | 1.25 |
| *C. perfringens* | 2.25 | 3.75 | 1.75 |
| *C. ramosum* | 1.25 | 1.75 | 0.5 |
| *Y. pseudotuberculosis* | 5.5 | 3.4 | 4.5 |
| Commensals | | | |
| *B. thetaiotaomicron* | 0.4 | 0.4 | 0.5 |
| *B. vulgatus* | 0.3 | 0.5 | 0.7 |

Strains F2064, F2076 and F1033 displayed significant inhibitory activity against *Candida albicans* and several potentially pathogenic bacteria. On the other hand, the strains displayed minimal activity against commensal strains commonly found in the indigenous gastrointestinal flora of the *Bacteroides* genus. Also, strains F2064, F2076 and F1033 did not display significant inhibitory activity among them. It is noteworthy that strain F1033 is the only strain displaying high inhibitory activity against *Campylobacter jejuni*, while strain F2076 outstands in inhibiting *Escherichia coli* and strain F2064 in inhibiting both *Candida albicans* and *Proteus mirabilis*.

6. Antioxidant Capacity

A) Methods

20 μl aliquots of overnight cultures of each strain ($10^9$ cfu/ml aprox) were placed in a 96-well plate. 200 μl of MRS supplemented with 10 mM of paraquat ($C_{12}H_{14}Cl_2N_2$, a superoxide anion donor) or 10 mM of sodium nitroprusside ($Na_2[Fe(CN)_5NO]$, a nitric oxide donor) were added to wells and plates incubated at 37° C. and 5% $CO_2$. Optical densities at 620 nm were read after 6 h. Results are expressed as percent of growth compared to growth in standard MRS medium. The same protocol was followed with the *L. rhamnosus* GG strain and the *L. plantarum* strain isolated from the commercial formulation VSL#3 (the isolation was performed using standard procedures).

B) Results

Oxidative stress is defined as an imbalance between generation of reactive oxygen species (ROS) and decreased antioxidant defence systems. Oxidative stress develops particularly in inflammatory reactions because the inflammatory cells, neutrophils, and macrophages produce large amounts of ROS (Rezaie A. et al., 2007; Roessner A. et al., 2008). Strains F1033, F2064 and F2076 showed a capacity to survive under strong oxidizing conditions comparable to the well-known probiotic strain *L. rhamnosus* GG, as well as to the *L. plantarum* strain isolated from the VSL#3 formula. It is worth noting that strain F2076 displayed the highest resistance both to paraquat (superoxide anion donor) and sodium nitroprusside (nitric oxide donor). Resistance to oxidative stress is a desirable trait for probiotic strains that are expected to survive in the environment of an inflamed mucosa.

TABLE 4

Percent of growth in medium containing 10 mM[ of paraquat or sodium nitroprusside, compared to standard MRS medium.

| Strain | % growth in paraquat | % growth in nitroprusside |
|---|---|---|
| *L. rhamnosus* GG | 70 ± 10 | 99 ± 17 |
| *L. plantarum* VSL#3 | 61 ± 4 | 88 ± 10 |
| F1033 | 67 ± 9 | 76 ± 22 |

TABLE 4-continued

Percent of growth in medium containing 10 mM of paraquat or sodium nitroprusside, compared to standard MRS medium.

| Strain | % growth in paraquat | % growth in nitroprusside |
|---|---|---|
| F2064 | 61 ± 18 | 67 ± 8 |
| F2076 | 72 ± 1 | 104 ± 19 |

7. Strain Genotyping

A) Methods

Strains F1033, F2064 and F2076 were subjected to a previously described protocol (Rodas A. M. et al., 2005) with minor modifications. Strains were grown on MRS agar plates and incubated at 37° C. 5% $CO_2$ for 18 h. Cells were harvested and washed 3 times in 8 ml PET (10 mM Tris pH 7.6, 1 M NaCl) then centrifuged at 6000 rpm 10 min. Pellets were resuspended in 700 ml lysis buffer (6 mM Tris, 1 M NaCl, 0.1 M EDTA, 0.5% SLS, 0.2% deoxycholic acid; 1 mg/ml lysozyme; 40 U/ml mutanolysin; 20 mg/ml RNase). An equal volume of 1.6% low melting point agarose (FMC BioProducts, Rockland, Me., USA) was added to the resuspended cells and solidification was allowed at 4° C. for 1 h. Inserts were transferred to 2 ml lysis buffer II (0.5 M EDTA pH 9.2, 1% N-lauryl sarcosine and 1 mg/ml pronase) and incubated at 50° C. for 48 h. Then inserts were washed at room temperature with TE buffer (10 mM Tris, 1 mM EDTA pH 8.0). Total DNA digestion was performed separately by Sfi-I and Sma-I restriction enzymes (Roche Diagnostics).

Pulse-field electrophoresis was carried out using CHEF DRIII apparatus (BioRad Laboratories). Inserts were loaded in a 1% agarose gel (SeaKem ME agarose, FMC BioProducts, ME, USA). DNA MW markers were Lambda ladder PFG Marker and Low Range PFG Marker (New England Biolabs). After electrophoresis, gels were stained with ethidium bromide and UV using GelDoc System (BioRad).

B) Results

FIG. 1 shows the pulse-field electrophoresis profiles obtained. Strain F1033 shows a similar genomic restriction profile to P. acidilactici R1001 after digestion with Sma-I. However, the genomic profile obtained after digestion with enzyme Not-I is clearly different. On the other hand, the genomic restriction profiles of strains F2064 and F2076 are clearly different among them and also compared both to L. plantarum 299v and to the L. plantarum strain contained in the VSL#3 formula.

8. Production of Short Chain Fatty Acids

A) Methods

Strains were incubated overnight in a basal medium (see TABLE 5) supplemented with different fibers, each one (inulin, pectin and FOS) in a specific amount, under microaerophilic conditions (5% $CO_2$) at 37° C. Next, cells were removed by centrifugation at 12.000 rpm for 10 min and supernatants were filtered and frozen in liquid nitrogen and kept at −80° C. until analyzed by gas chromatography, focusing on the amount of acetic, propionic and butyric acids.

TABLE 5

| COMPOUND | CONCENTRATION |
|---|---|
| Peptone | 2 g/L |
| Yeast extract | 2 g/L |
| NaCl | 0.1 g/L |
| K2HPO4 | 0.04 g/L |

TABLE 5-continued

| COMPOUND | CONCENTRATION |
|---|---|
| KH$_2$PO$_4$ | 0.04 g/L |
| MgSO$_4$·7H$_2$O | 0.01 g/L |
| CaCl$_2$·6H$_2$O | 0.01 g/L |
| NaHCO$_3$ | 2 g/L |
| Hemin | 0.05 g/L |
| HCl Cysteine | 0.5 g/L |
| Bile Salt | 0.5 g/L |
| Tween 80 | 2 g/L |
| Vitamin K1 | 10 µl |
| Inulin | 10 g/L |
| Pectin | 10 g/L |
| FOS | 10 g/L |

B) Results

Short chain fatty acids (SCFAs) are the end products of anaerobic bacteria break down of carbohydrates in the large bowel. SCFAs, mainly acetate, propionate and butyrate account for approximately 80% of the colonic anion concentration and are produced in nearly constant molar ratio 62:22:15. Among their various properties, SCFAs, especially butyric acid, but also acetic and propionic acid, are readily absorbed by intestinal mucosa, are relatively high in caloric content, are metabolized by colonocytes and hepatocytes, stimulate sodium and water absorption in the colon and are trophic to the intestinal mucosa (D'Argenio G. et al., 1999). On the other hand, high amounts of acetic acid have long been known to be irritant to the intestinal mucosa (Yamada Y. et al., 1992). Strains F1033, F2064 and F2076 are strong producers of either acetic, propionic or butyric acid.

TABLE 6

Acetic, propionic and butyric acid production by strains grown on basal medium enriched with inulin, pectin and FOS.

| Strain | Acetic (mg/ml) | Propionic (mg/ml) | Butyric (mg/ml) |
|---|---|---|---|
| L. rhamnosus GG | n.d | n.d | 7.7 |
| F1033 | n.d | n.d | 21.4 |
| F2064 | n.d | 30.2 | 9.7 |
| F2076 | 46.5 | n.d | n.d |

(n.d. = non-detected)

9. Compatibility with IBD Treatments

A) Method

Supplemented broth was prepared by dissolving 5-aminosalycilic acid (Pentasa®, Ferring Pharmaceuticals) at the maximal soluble concentration (0.84 gr/L) and half this concentration (0.42 gr/L) in MRS liquid broth. The strains of the invention were grown in standard MRS broth or 5-aminosalicylic acid-supplemented broth for 4 h at 37° C. in microaerophilic conditions (5% $CO_2$), and growth was assessed by measuring optical density at 620 nm. Results are expressed as percent of growth in standard MRS medium.

B) Results

Prolonged treatment of mild to moderate IBD symptoms is usually carried out using oral aminosalycilates (5-ASA derivatives) (Katz J. A., 2007). Therefore it is of interest to evaluate if the probiotic strains of the invention can be co-administered with 5-ASA derivatives. Considering that growth of none of said strains is completely inhibited despite the high stringency of the conditions, we can conclude that co-administration of mesalazine is not likely to compromise the efficacy of the probiotic, even using saturated concentrations of mesalazine (0.84 g/L) as shown in TABLE 7:

TABLE 7

|  | 4 h (% of growth) | | 8 h (% of growth) | |
| --- | --- | --- | --- | --- |
|  | 0.42 g/L | 0.84 g/L | 0.42 g/L | 0.84 g/L |
| VSL#3 | 56.2 | 38.1 | 43.2 | 35.1 |
| F1033 | 72.7 | 60.6 | 51.8 | 42.3 |
| F2064 | 59.7 | 48.0 | 62.3 | 55.1 |
| F2076 | 51.6 | 22.1 | 50.2 | 22.5 |

10. In Vivo Effect on Chemically-induced Gut Inflammation

A) Methods

The therapeutic effect of the composition of the invention on mild gut inflammation was investigated with a 5-day repetitive oral administration of dextran sodium sulfate (DSS) in the mouse (Okayasu I. et al., 1990). When used in a low dose (2.5-3%) for a short time (5 days), DSS produces mild colitis, with intestinal inflammation at the histological level but without significant macroscopic changes (e.g. colon shortening, mesenteric adherences).

External symptoms include weight loss and diarrhea, with rare occurrence of blood in feces. Therefore this model is representative of low-grade ulcerative colitis.

Strains F1033, F2064 and F2076 were lyophilised in sterile water with 15% skim milk and 4% sucrose as cryoprotectants and mixed in equal amounts (ratio in concentration 1:1:1).

Eight-week-old Balb/c mice (Charles River, Barcelona, Spain), weighing 20-25 g, were kept under specific pathogen-free (SPF) conditions in an isolator (Harlan Iberica, Barcelona, Spain) at constant temperature (22° C.) in a 12-hour of light/dark cycle. Two mice acted as littermates. Mice had free access to sterilized diets (laboratory's standard diet; Harlan Iberica, Barcelona, Spain) and to drinking fluid. Mice were kept for 7 days in the facility before the beginning of the experiments (quarantine). Mice were allocated to one of four groups: a) probiotic composition of the invention+DSS (n=8); b) VSL#3 (VSL Pharmaceuticals, USA)+DSS (n=8); c) vehicle+DSS (n=8); and d) vehicle+healthy controls (n=6).

Probiotics (or vehicle) were administered by oral gavage for ten days before (day −10) starting DSS administration (day 0). Each mouse received daily $2.5 \times 10^8$ cfus of probiotic in 0.1 mL of sterilized water (vehicle) by gavage. Non-probiotic treated mice received the same volume of vehicle (distilled water with 15% skim milk and 4% sucrose).

Mice were fed with 3% (w/v) DSS (mol. Wt 40 kD, Applichem Lifescience, VWR, Barcelona) in their drinking water for 5 days (days 0 to 4, followed by three days without DSS) according to a previously described method with minor modifications (Okayasu I, et al. Gastroenterol 1990). Healthy controls never received DSS.

Clinical signs were daily monitored. Disease Activity Index was calculated according to the following formula and interpretation table:

$$DAI = Score_{Weight\ Loss} + Score_{Stool\ Blood} + Score_{Stool\ Consistency}$$

Results are shown in TABLE 8:

TABLE 8

| Weight Loss | Score | Stool Blood | Score | Stool Consistency | Score |
| --- | --- | --- | --- | --- | --- |
| <1% | 0 | Absence | 0 | Formed and hard | 0 |
| 1-5% | 1 |  |  | Formed but soft | 1 |
| 5-10% | 2 | Presence | 2 | Loose stools | 2 |
| 10-15% | 3 |  |  | Mild diarrhea (watery) | 3 |
| >15% | 4 | Gross bleeding | 4 | Gross diarrhea | 4 |

The Disease Activity Index score used hereby was first described by Cooper et al. and combines several clinical symptoms into one normalized score (Cooper H. S. et al., 1993). Maximum score is 12 points. This score has been widely used to evaluate the efficacy of experimental treatments—probiotics among them—in animal models of IBD (Fitzpatrick L. R. et al., 2007; Grabig A. et al., 2006; Sasaki M. et al., 2005).

After being sacrificed by anesthetic overdose of inhaled Halothane (Fluotane®, Zeneca Ltd, UK), colon samples of the animals were harvested and washed in cold PBS. Colon weight/length ratio was recorded. Samples for cytokine measurements were frozen in liquid nitrogen and homogenized in 1 mL of cold PBS with inhibitor protein cocktail (Sigma-Aldrich Chem., Spain) and centrifuged (15000× g, 10 min). IL-6, IL-10, IL23p19, IFN-γ and TNF-α concentrations were measured in colonic supernatants using Cytokine 6-Plex Assay (Procarta™ Cytokine Profiling Kit, PANOMICS, Spain) for the Luminex® Platform (Luminex® Co, Austin, USA). Fluorescent microparticle beads, pre-spotted with cytokine-specific antibodies, were incubated with 50 μL 1:5 diluted supernatant. Specific-biotinylated secondary antibodies and streptavidin-phycoerythrin (S-PE) were sequentially added. Data were expressed as pg of cytokine per mg of protein (Quick Start Bradford Protein Assay, BIO-RAD, CA, USA). All measurements were done in duplicate.

B) Results

Disease Activity Index

Figure 2:
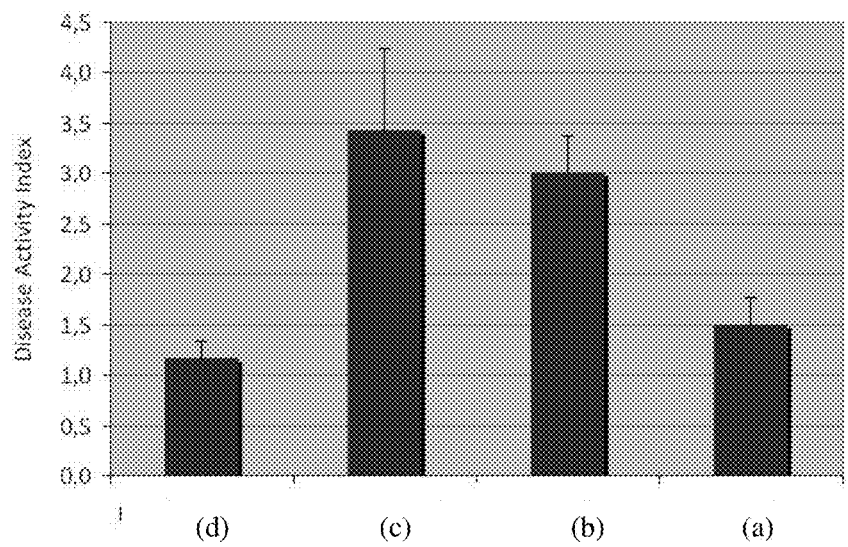
FIG. 2 represents the Disease Activity Index (Y-axis) in a group of mice suffering from a DSS-induced intestinal inflammation. X-axis represents the administration of: a, probiotic formulation of the invention in a group of mice suffering from a DSS-induced intestinal inflammation; b, a commercial probiotic formulation (VSL#3) in a group of mice suffering from a DSS-induced intestinal inflammation; c, vehicle in a group of mice suffering from a DSS-induced intestinal inflammation; and d, vehicle in a healthy control group. This figure refers to the "In Vivo Effect on Chemically-induced Gut Inflammation" section.

As shown in FIG. 2, the group receiving the probiotic formula of the invention displayed a significant improvement of the clinical symptoms when compared to DSS-treated controls, as assessed by the Disease Activity Index (p<0.05, two-tail ANOVA with Tukey-Kramer post-hoc test). Healthy controls also displayed a lower Disease Activity Index (p<0.05).

Cytokine Levels

Figure 3:
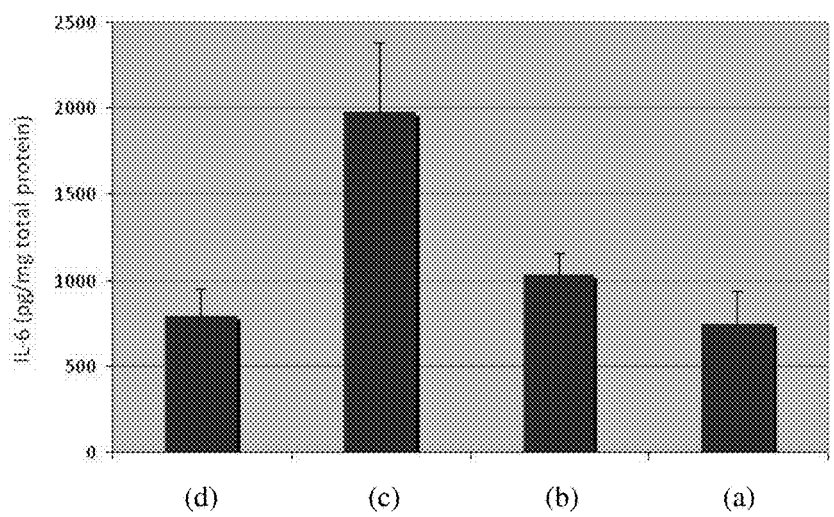
FIG. 3 represents the levels of IL-6 (Y-axis) in a group of mice suffering from a DSS-induced intestinal inflammation. X-axis represents: a, probiotic formulation of the invention administered to a group of mice suffering from a DSS-induced intestinal inflammation; b, a commercial probiotic formulation (VSL#3) administered to a group of mice suffering from a DSS-induced intestinal inflammation; c, vehicle administered to a group of mice suffering from a DSS-induced intestinal inflammation; and d, vehicle in a healthy control group. This figure refers to the "In Vivo Effect on Chemically-induced Gut Inflammation" section.

Analysis of various cytokines in the intestinal mucosa revealed that probiotic formula of the invention significantly decreased IL-6 when compared to DSS-treated controls (p<0.01, two-tail ANOVA with Tukey-Kramer post-hoc test), while the effect of commercial probiotic formula VSL#3 failed to achieve significance (p>0.05). IL-6 is a marker of acute inflammation (FIG. 3). As expected, levels of IL-6 in healthy controls were also significantly lower than DSS-treated controls (p<0.05). A statistically significant correlation was found between clinical symptoms (DAI score) and IL-6 levels in the intestinal mucosa (p<0.05, Spearman ranks test) (data not shown). On the other hand, correlation between clinical symptoms and IL-10, IL-23, TNFα or IFNγ was not statistically significant, and the probiotic formula of the invention did not significantly affect the levels of these cytokines.

11. In Vivo Effect on Spontaneous Gut Inflammation

A) Methods

The therapeutic effect of probiotic formula of the invention was also investigated in the IL-10 knock-out mouse model. This model spontaneously develops bowel inflammation at 8 to 12 weeks of age, with a penetrance of 80-90%

(Scheinin T. et al., 2003). Interleukin 10 (IL-10) is an important regulatory cytokine that supresses effector functions of macrophage/monocytes, T helper 1 (Th1) cells, and natural killer cells. In addition, IL-10 augments proliferation and differentiation of B cells. Murine models lacking the IL-10 gene spontaneously develop inflammatory bowel disease and gastrointestinal tumors. The gastrointestinal flora has been implicated in the pathogenesis of these disease states as germ free animals do not develop disease. The IL-10 knock-out mouse has been widely used to evaluate new therapeutic options for IBD.

Six-week-old C57B6J IL-10-deficient or wild type mice (Charles River, Barcelona, Spain) were kept under specific pathogen-free (SPF) conditions in an isolator (Harlan Ibérica, Barcelona, Spain) at constant temperature (22° C.) in a 12-hour of light/dark cycle. Mice had free access to sterilized diets (diet based in AIN-93 for maintenance of mice was composed by 12% of water, 14.5% of protein, 4% of fat, 4.5% of fibre and 4.7% of ash; Harlan Interfauna Ibérica S. A., Barcelona, Spain) and to drinking fluid.

Mice were allocated to one of three groups: a) probiotic formula I.3.1 (n=12 IL-10−/−; n=5 wild type); b) VSL#3 (n=12 IL-10−/−; n=5 wild type); and c) vehicle (n=12 IL-10−/−; n=5 wild type). Each mouse in groups "a" and "b" received daily $10^9$ CFU of probiotic in sterilized drinking water (vehicle). Non-probiotic treated mice (Placebo group) received vehicle alone. Probiotics (or vehicle) were administered during ten weeks. Clinical signs were daily monitored. Disease Activity Index (Cooper H. S. et al., 1993) was calculated as in the model of DSS-induced gut inflammation (see above).

Sixteen-weeks-old mice were sacrificed by anaesthetic overdose of inhaled Halothane (Fluotane®, Zeneca Ltd, UK). Colon samples of the animals were harvested and washed in cold PBS. Blood samples were also collected by cardiac puncture to analyze hematocrit and hemoglobin concentration (Coulter MaxM Analyzer with autoloader, Izasa, Spain). Colon weight/length ratio was recorded. Then, colons were frozen in liquid nitrogen and cytokines IL-6, and IFNγ were measured using the same protocol as in the model of DSS-induced gut inflammation (see above).

B) Results

Disease Activity Index

Figure 4:
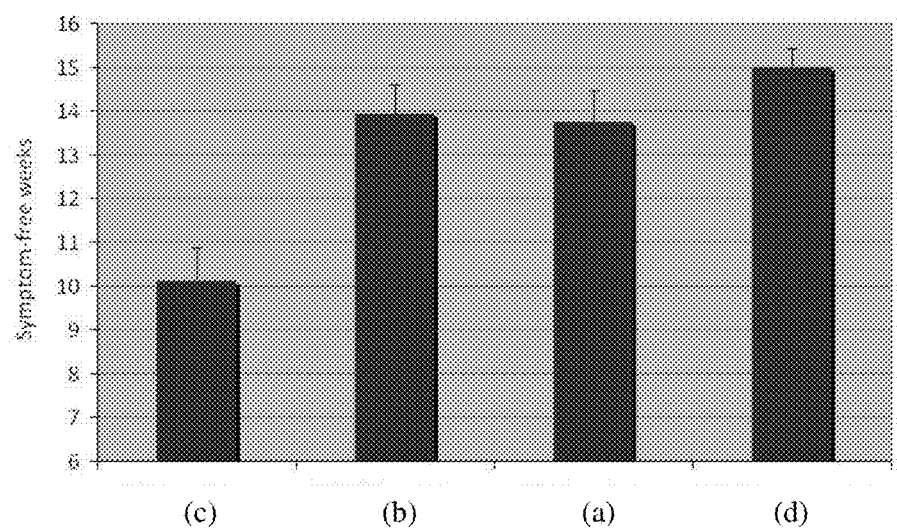
FIG. 4 represents the number of Symptom-free weeks (i.e. number of weeks before the onset of the first symptom, thus being the Disease Activity Index equal to zero) (Y-axis) in a IL-10 knock-out mouse model. X-axis represents the administration of: a, the probiotic composition of the invention to a IL-10 knock-out mice group; b, the commercial probiotic formulation VSL#3 to a IL-10 knock-out mice group; c, PBS to a IL-10 knock-out mice group; and d, vehicle in a healthy control group. This figure refers to the "In Vivo Effect on Spontaneous Gut Inflammation" section.

As shown in FIG. 4, a significant delay on the onset of the clinical symptoms was observed both in the group treated with the composition of the invention and the VSL#3 commercial formula when compared to vehicle-treated controls ($p<0.01$, two-tail ANOVA with Tukey-Kramer post-hoc test). Additionally, treated groups tended to display lower Disease Activity Index scores, although the difference did not reach significance (data not shown).

Cytokine Levels

Figure 5:
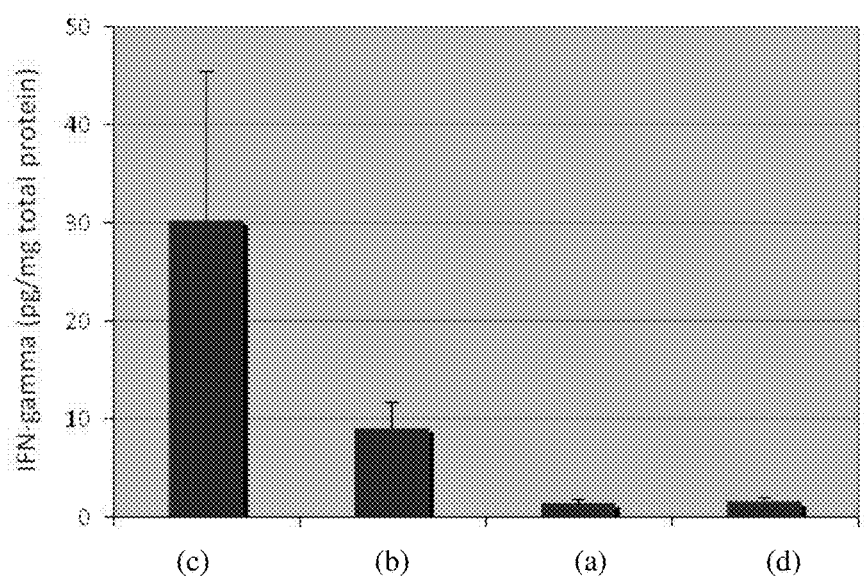
FIG. 5 represents the levels of IFN-γ (Y-axis) in a IL-10 knock-out mouse model. X-axis represents: a, probiotic formulation of the invention to a IL-10 knock-out mice group; b, a commercial probiotic formulation (VSL#3) to a IL-10 knock-out mice group; c, vehicle to a IL-10 knock-out mice group; and d, vehicle to a healthy control group. This figure refers to the "In Vivo Effect on Chemically-induced Gut Inflammation" section.
Figure 6:
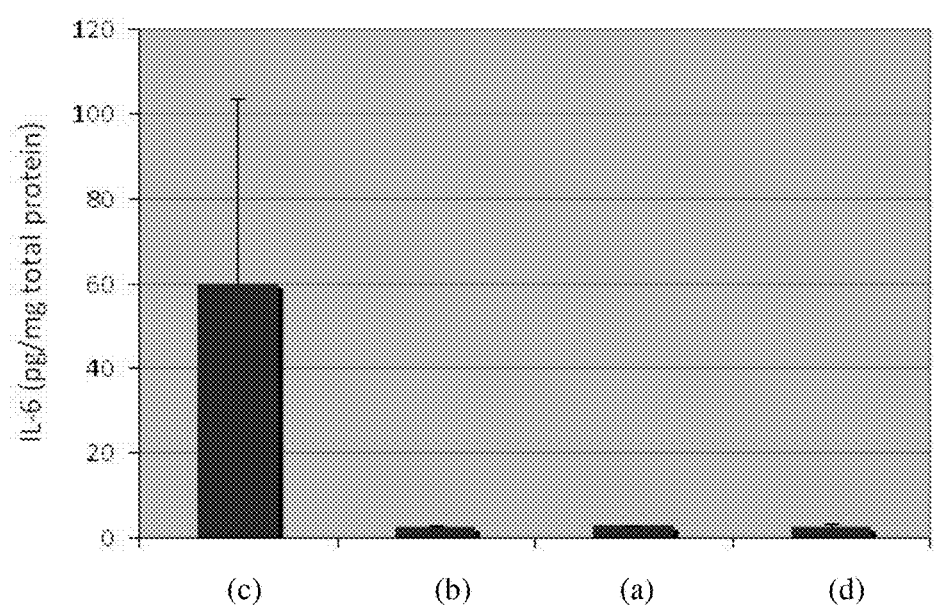
FIG. 6 represents the levels of IL-6 (Y-axis) in a IL-10 knock-out mouse model. X-axis represents: a, probiotic formulation of the invention to a IL-10 knock-out mice group; b, a commercial probiotic formulation (VSL#3), to a IL-10 knock-out mice group; c, vehicle administered to a IL-10 knock-out mice group; and d, vehicle to a healthy control group. This figure refers to the "In Vivo Effect on Chemically-induced Gut Inflammation" section.

Analysis of various cytokines revealed that probiotic composition of the invention significantly decreased IFNγ levels in knockout mice when compared both to vehicle-treated knock-outs ($p<0.01$, two-tail nonparametric ANOVA with Dunn post-hoc test) and to commercial formula VLS#3 ($p<0.05$). In fact, as it is shown in FIG. 5, the levels of IFNγ attained the same levels as those of wild-type healthy controls. Additionally, as it is derived from FIG. 6, there was also a clear tendency of probiotic formulas to reduce the levels of IL-6, although results did not reach significance due to the large standard deviation among vehicle knockout mice.

A significant correlation was found between the severity of clinical symptoms (Disease Activity Index) and the levels of IFNγ at the end of the study in colonic mucosa measured after the sacrifice ($p<0.05$, Spearman rank's test) (data not shown).

Safety of the Probiotic Formula

Clinical signs (weight loss, altered behavior, fur aspect, diarrhoea and stool blood) were daily monitored in wild-type mice receiving daily doses of the probiotic formula of the invention, the VSL#3 formula or vehicle during 10 weeks. No morbidity signs were detected during the study. Upon sacrifice, animals were subjected to gross necropsy. Analysis of all major cavities and organs did not reveal any pathological alteration (data not shown).

12. In Vivo Efficacy on IBS Subjects

A) Methods

Study Design

A multicenter randomized, double-blind, placebo-controlled clinical trial to study the effect of the composition of the invention on IBS patients was conducted.

Hydroxymethyl propyl cellulose capsules were filled with: (1) 150 mg of maltodextrin, (2) 5 mg of magnesium stearate, (3) 5 mg of silicon dioxide and (4) 200 mg of a 1:1:1 mixture of the three strains of the invention (at a concentration $5·10^{10}$ cfus/capsule). In addition a placebo was made with the same list of excipients and amounts but without including the composition of the invention. Content of the capsules throughout the study ranged from $5·10^{10}$ to $1·10^{10}$ cfus.

33 eligible adult patients of both sexes meeting Rome III criteria for irritable bowel syndrome (Longstreth G. F. et al., 2006) were enrolled and randomly allocated to one of the following treatments for 6 weeks: a) the capsule including the composition of the invention once daily (n=18); and b) the placebo capsule once daily (n=15). The study was conducted according to the Helsinki Declaration for Clinical Trials and approved by the appropriate Ethical Committee.

Efficacy Assessment

Figure 7:
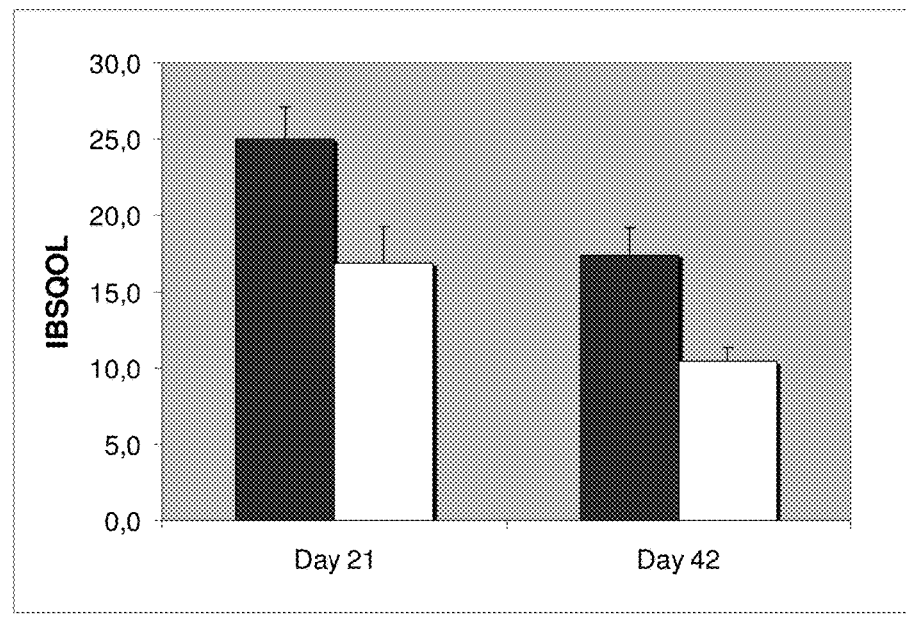
FIG. 7 represents the variation of the IBSQoL score compared to baseline (Y-axis) of volunteers treated with capsules including the composition (black bars) or placebo (white bars). X-axis represents the variation of the score 21 days and after 42 days of treatment. This figure refers to the "Improvement of Health-Related Quality of Life" in the "In Vivo Efficacy on IBS Subjects" section.
Figure 8:
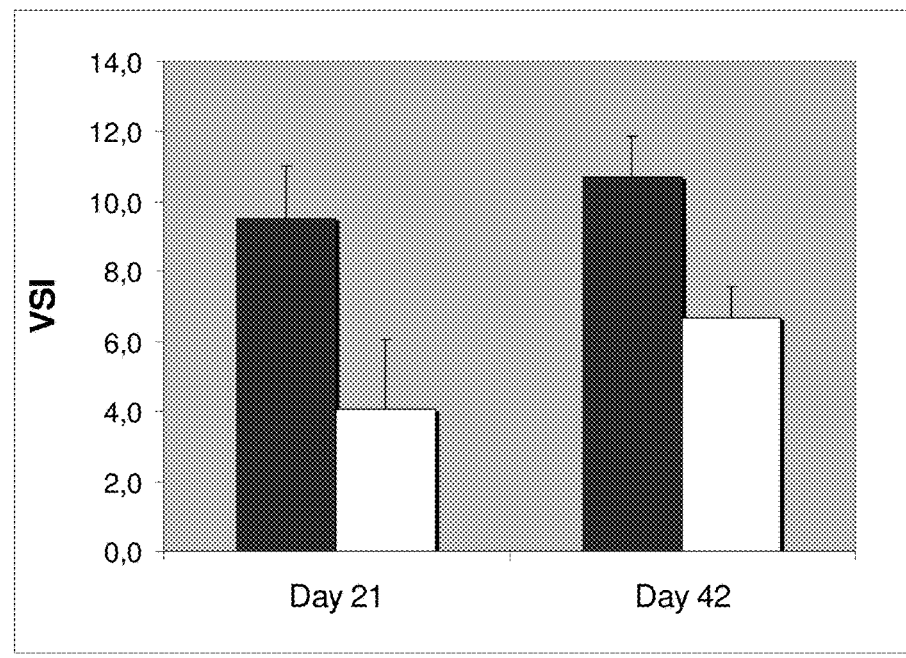
FIG. 8 represents the variation of the VSI score compared to baseline (Y-axis) of volunteers treated with capsules including the composition (black bars) or placebo (white bars). X-axis represents the variation of the score after three weeks and after six weeks of treatment. This figure refers to the "Improvement of the Visceral Sensitivity" in the "In Vivo Efficacy on IBS Subjects" section.

The primary endpoint of this study was the global effect on health-related quality of life (hereinafter also referred as "HRQOL"), as assessed using a specific questionnaire for IBS: the validated Spanish version of the IBSQOL questionnaire (Badia X. et al., 2000). Following the guidelines from the Spanish Gastroenterology Association, scores were standardized to a 0-100 scale. The secondary endpoint was the assessment of anxiety related to gastrointestinal sensations and symptoms by means of the validated Visceral Sensitivity Index questionnaire (hereinafter also referred as "VSI") (Labus J. S. et al., 2004). Volunteers were asked to fill these questionnaires at baseline (day 1), on day 21 and on day 42. Data was assessed per intent to treat analysis. The results are shown in FIGS. 7 and 8.

B) Results

Baseline Characteristics

No significant differences were evident between the groups in terms of baseline characteristics, as can be seen in Table 9, indicating that subjects in both groups were comparable in terms of the variables assessed. Groups were also comparable in terms of baseline standard blood biochemical parameters, anthropometric parameters, age and sex.

TABLE 9

Baseline scores for the two treatment groups

| Group | Capsule including the composition of the invention | Placebo (n = 15) |
|---|---|---|
| IBSQOL | 45.7 ± 7.9 | 48.2 ± 19.2 |
| VSI | 34.9 ± 13.3 | 41.2 ± 11.8 |

Improvement of Health-related Quality of Life (FIG. 7)

The composition of the invention significantly improved health-related quality of life compared to placebo when assessed both after 21 days and 42 days of treatment (p<0.05, T-test). Therefore, it is demonstrated that the composition of the present invention significantly reduces morbility and improves the quality of life of IBS subjects well above the placebo effect. The positive effects of the composition include the food-related distress, anxiety, interference in daily activities and sleep disturbance domains of the HRQOL questionnaire. The improvements in these scales suggest a reduction in abdominal pain, discomfort and altered bowel habits. To our knowledge, this is the first time that it is shown a probiotic composition displaying a significant effect on the global health-related quality of life of IBS patients.

Improvement in the Visceral Sensitivity Index (FIG. 8)

The composition of the present invention significantly reduced the gastrointestinal symptom-specific visceral sensitivity of IBS subjects compared to placebo. The effect was close to significant after 21 days of treatment, and clearly significant after 42 days of treatment (p<0.01, T-test), further confirming the usefulness of the composition of the present invention in treating IBS. The most pronounced improvement was observed in abdominal discomfort and bloating-related items of the questionnaire. Particularly, TABLE 10 shows the numbers of subjects reporting a significant improvement related to bloating and distension (as defined by an increase of at least two points compared to baseline in the 6-point scale of the VSI questionnaire that measures bloating and distension-related anxiety) at the end of the treatment. The difference between the two groups is statistically significant (p<0.05, Fisher's exact test).

TABLE 10

Effect on abdominal bloating and distension-related anxiety, according to the VSI questionnaire, after 42 days of treatment

| Bloating and distension-related anxiety | Capsule including the composition of the invention (n = 18) | Placebo (n = 15) |
| --- | --- | --- |
| Subjects reporting an improvement compared to baseline | 7 | 1 |
| Subjects not reporting an improvement compared to baseline | 11 | 14 |

From the results obtained, therefore it is concluded that the composition of the invention is effective in treating abdominal distension and bloating.

13. Effect on Abdominal Bloating and Reduced Bowel Movements

A 25 years old woman was suffering from chronic abdominal bloating and altered intestinal motility, reporting sometimes as few as on bowel movement per week. Diagnostic revealed a hypotonic and hypokinetic stomach, without evidence of other structural alterations in the gastrointestinal tract.

The patient undertook a treatment of one capsule per day (as those described in example 12). After one week of treatment the patient reported a significant reduction of abdominal bloating and distension and a normalization of bowel habits. Symptoms reappeared after stopping the treatment for a few days. After restarting of the treatment in the form of one capsule every two days, the patient reported again a noticeable and long-lasting positive effect both on bloating and bowel habits.

This example further supports the use of the composition of the invention to treat abdominal bloating and altered intestinal motility in subjects which are not classified as having Irritable Bowel Syndrome.

BIBLIOGRAPHIC REFERENCES

Altschul, S. F., et al. "Basic local alignment search tool", *J. Mol. Biol.,* 1990, vol. 215, p. 403-410.

Anadón, A., et al. "Opinion of the Scientific Panel on Additives and Products or Substances used in Animal Feed on the updating of the criteria used in the assessment of bacteria for resistance to antibiotics of human veterinary importance", *The EFSA Journal,* 2005, vol. 233, p. 1-12.

Andreoletti, O., et al. "The maintenance of the list of QPS microorganisms intentionally added to food or feed. Question no: EFSA-Q-2008-006", The EFSA Journal, 2008, vol. 923, p. 1-48.

Araya, M., et al. (2002) Guidelines for the Evaluation of Probiotics in Food—Joint FAO/WHO Working Group. FAO/WHO, Ontario, Canada.

Badia, X., et al. "Adaptación al español del cuestionario IBSQoL para la medición de la calidad de vida en pacientes con síndrome de intestino irritable.", Rev Esp Enferm Dig, 2000, vol. 92, p. 637-643.

Bories, G., et al. "Update on the criteria used in the assessment of bacterial resistance to antibiotics of human or veterinary importance", *The EFSA Journal,* 2008, vol. 732, p. 1-15.

Collado, M., et al. "Probiotic Strains and Their Combination Inhibit In Vitro Adhesion of Pathogens to Pig Intestinal Mucosa", *Current Microbiology,* 2007, vol. 55, p. 260-265.

Cooper, H. S., et al. "Clinicopathologic study of dextran sulfate sodium experimental murine colitis", *Lab Invest.,* 1993, vol. 69, p. 238-249.

D'Argenio, G. and Mazzacca, G. "Short-chain fatty acid in the human colon. Relation to inflammatory bowel diseases and colon cancer", *Adv Exp Med Biol,* 1999, vol. 472, p. 149-158.

Daniel, C., et al. "Selecting Lactic Acid Bacteria for Their Safety and Functionality by Use of a Mouse Colitis Model", *Appl. Environ. Microbiol.,* 2006, vol. 72, p. 5799-5805.

Dean, B. B., et al. "Impairment in work productivity and health-related quality of life in patients with IBS", *Am J Manag Care.,* 2005, vol. 11, p. S17-26.

Fitzpatrick, L. R., et al. "Effects of the probiotic formulation VSL#3 on colitis in weanling rats", *J Pediatr Gastroenterol Nutr.,* 2007, vol. 44, p. 561-570.

Fukumoto, S., et al. "Short-chain fatty acids stimulate colonic transit via intraluminal 5-HT release in rats", *Am J Physiol Regul Integr Comp Physiol,* 2003, vol. 284, p. R1269-1276.

Grabig, A., et al. "*Escherichia coli* Strain Nissle 1917 Ameliorates Experimental Colitis via Toll-Like Receptor 2- and Toll-Like Receptor 4-Dependent Pathways", *Infect. Immun.,* 2006, vol. 74, p. 4075-4082.

Guarner, F. and Schaafsma, G. J. "Probiotics", *Int J Food Microbiol.,* 1998, vol. 39, p. 237-238.

Jacobsen, C. N., et al. "Screening of Probiotic Activities of Forty-Seven Strains of *Lactobacillus* spp. by In Vitro Techniques and Evaluation of the Colonization Ability of Five Selected Strains in Humans", *Appl. Environ. Microbiol.*, 1999, vol. 65, p. 4949-4956.

Katz, J., A. "Management of inflammatory bowel disease in adults", *Journal of Digestive Diseases,* 2007, vol. 8, p. 65-71.

Labus, J. S., et al. "The Visceral Sensitivity Index: development and validation of a gastrointestinal symptom-specific anxiety scale", *Alimentary Pharmacology & Therapeutics,* 2004, vol. 20, p. 89-97.

Longstreth, G. F., et al. "Functional Bowel Disorders", *Gastroenterology,* 2006, vol. 130, p. 1480-1491.

Maslowski, K. M., et al. "Regulation of inflammatory responses by gut microbiota and chemoattractant receptor GPR43", *Nature,* 2009, vol. 461, p. 1282-1286.

Okayasu, I., et al. "A novel method in the induction of reliable experimental acute and chronic ulcerative colitis in mic", *Gastroenterology.,* 1990, vol. 98, p. 694-702.

Pathmakanthan, S., et al. "*Lactobacillus plantarum* 299: Beneficial in vitro immunomodulation in cells extracted from inflamed human colon", *Journal of Gastroenterology and Hepatology,* 2004, vol. 19, p. 166-173.

Rezaie, A., et al. "Oxidative Stress and Pathogenesis of Inflammatory Bowel Disease: An Epiphenomenon or the Cause?", *Digestive Diseases and Sciences,* 2007, vol. 52, p. 2015-2021.

Rodas, A. M., et al. "Polyphasic study of wine *Lactobacillus* strains: taxonomic implications", *Int J Syst Evol Microbiol,* 2005, vol. 55, p. 197-207.

Roessner, A., et al. "Oxidative stress in ulcerative colitis-associated carcinogenesis", *Pathol Res Pract.,* 2008, vol. 204, p. 511-524.

Sasaki, M., et al. "Reversal of experimental colitis disease activity in mice following administration of an adenoviral IL-10 vector", *Journal of Inflammation,* 2005, vol. 2, p. 13.

Scheinin, T., et al. "Validation of the interleukin-10 knock-out mouse model of colitis: antitumour necrosis factor-antibodies suppress the progression of colitis.", *Clin Exp Immunol,* 2003, vol. 133, p. 38-43.

Tazoe, H., et al. "Roles of short-chain fatty acids receptors, GPR41 and GPR43 on colonic functions", *J Physiol Pharmacol.,* 2008, vol. 59, p. 251-262.

Tedelind, S., et al. "Anti-inflammatory properties of the short-chain fatty acids acetate and propionate: a study with relevance to inflammatory bowel disease", *World J Gastroenterol.,* 2007, vol. 13, p. 2826-2832.

Vanhoutvin, S. A., et al. "The effects of butyrate enemas on visceral perception in healthy volunteers", *Neurogastroenterology & Motility,* 2009, vol. 21, p. 952-e976.

Wang, Q., et al. "Naive Bayesian Classifier for Rapid Assignment of rRNA Sequences into the New Bacterial Taxonomy", *Appl. Environ. Microbiol.,* 2007, vol. 73, p. 5261-5267.

Weisburg, W. G., et al. "16S ribosomal DNA amplification for phylogenetic study", *J. Bacteriol.,* 1991, vol. 173, p. 697-703.

Yamada, Y., et al. "A comparative analysis of two models of colitis in rats", *Gastroenterology,* 1992, vol. 102, p. 1524-1534.

Zhang, L., et al. "Alive and Dead *Lactobacillus rhamnosus* GG Decrease Tumor Necrosis Factor-alpha-Induced Interleukin-8 Production in Caco-2 Cells", *J. Nutr.,* 2005, vol. 135, p. 1752-1756.

WO96/29083
EP 554418
EP 415941
U.S. Pat. No. 7,195,906

The invention claimed is:

1. A method of treating abdominal distension and bloating, comprising administering to a patient in need thereof a therapeutically effective amount of an ingestible probiotic composition comprising at least one strain selected from the group consisting of:
   (a) from about $10^5$ cfu to about $10^{12}$ cfu of the isolated strain of *Lactobacillus plantarum* deposited in the Spanish Type Culture Collection (CECT) under the accession number CECT 7484, per gram weight of the composition;
   (b) from about $10^5$ cfu to about $10^{12}$ cfu of the isolated strain of *Lactobacillus plantarum* deposited in the Spanish Type Culture Collection (CECT) under the accession number CECT 7485, per gram weight of the composition; and
   (c) from about $10^5$ cfu to about $10^{12}$ cfu of the isolated strain of *Pediococcus acidilactici* deposited in the Spanish Type Culture Collection (CECT) under the accession number CECT 7483, per gram weight of the composition.

2. The method of claim 1, wherein the isolated strain has been cultivated in a suitable culture medium and post-treated after cultivation to obtain a biologically pure culture, and wherein the resulting biologically pure culture is in the form of a liquid or solid.

3. The method of claim 2, wherein the post-treatment is freeze drying.

4. The method of claim 1, wherein the composition further comprises at least one pharmaceutically acceptable excipient.

5. The method of claim 1, wherein the composition further comprises at least one veterinary acceptable excipient.

6. The method of claim 1, wherein the composition further comprises at least one edible ingredient.

7. The method of claim 6, wherein the composition is a dietary supplement.

8. A method of treating inflammatory bowel conditions or disorders comprising administering to a patient in need thereof a therapeutically effective amount of an ingestible probiotic composition comprising at least one strain selected from the group consisting of:
   (a) from about $10^5$ cfu to about $10^{12}$ cfu of the isolated strain of *Lactobacillus plantarum* deposited in the Spanish Type Culture Collection (CECT) under the accession number CECT 7484, per gram weight of the composition;
   (b) from about $10^5$ cfu to about $10^{12}$ cfu of the isolated strain of *Lactobacillus plantarum* deposited in the Spanish Type Culture Collection (CECT) under the accession number CECT 7485, per gram weight of the composition; and
   (c) from about $10^5$ cfu to about $10^{12}$ cfu of the isolated strain of *Pediococcus acidilactici* deposited in the Spanish Type Culture Collection (CECT) under the accession number CECT 7483, per gram weight of the composition.

9. The method of claim 8, wherein the bowel condition or disorder is bowel inflammation.

10. The method of claim 8, wherein the bowel condition or disorder is Inflammatory Bowel Disease.

11. The method of claim 8, wherein the isolated strain has been cultivated in a suitable culture medium and post-treated after cultivation to obtain a biologically pure culture, and wherein the resulting biologically pure culture is in the form of a liquid or solid.

12. The method of claim 11, wherein the post-treatment is freeze drying.

13. The method of claim 8, wherein the composition further comprises at least one pharmaceutically acceptable excipient.

14. The method of claim 8, wherein the composition further comprises at least one veterinary acceptable excipient.

15. The method of claim 8, wherein the composition further comprises at least one edible ingredient.

16. The method of claim 15, wherein the composition is a dietary supplement.

17. A method of treating Irritable Bowel Syndrome or disorders with similar symptoms comprising administering to a patient in need thereof a therapeutically effective amount of an ingestible probiotic composition comprising at least one strain selected from the group consisting of:
   (a) from about $10^5$ cfu to about $10^{12}$ cfu of the isolated strain of *Lactobacillus plantarum* deposited in the Spanish Type Culture Collection (CECT) under the accession number CECT 7484, per gram weight of the composition;
   (b) from about $10^5$ cfu to about $10^{12}$ cfu of the isolated strain of *Lactobacillus plantarum* deposited in the Spanish Type Culture Collection (CECT) under the accession number CECT 7485, per gram weight of the composition; and
   (c) from about $10^5$ cfu to about $10^{12}$ cfu of the isolated strain of *Pediococcus acidilactici* deposited in the Spanish Type Culture Collection (CECT) under the accession number CECT 7483, per gram weight of the composition.

18. The method of claim 17, wherein the isolated strain has been cultivated in a suitable culture medium and post-treated after cultivation to obtain a biologically pure culture, and wherein the resulting biologically pure culture is in the form of a liquid or solid.

19. The method of claim 18, wherein the post-treatment is freeze drying.

20. The method of claim 17, wherein the composition further comprises at least one pharmaceutically acceptable excipient.

21. The method of claim 17, wherein the composition further comprises at least one veterinary acceptable excipient.

22. The method of claim 17, wherein the composition further comprises at least one edible ingredient.

23. The method of claim 22, wherein the composition is a dietary supplement.

* * * * *